US011013685B2

(12) United States Patent
Bruun et al.

(10) Patent No.: US 11,013,685 B2
(45) Date of Patent: *May 25, 2021

(54) CANNABINOID CHEWING GUM WITH IMPROVED RELEASE OF CANNABINOIDS

(71) Applicant: NordicCan A/S, Vejle (DK)

(72) Inventors: Heidi Ziegler Bruun, Vejle Ost (DK); Dorthe Schackinger Boesen, Vejle (DK); Ane Eriksen, Vejle (DK)

(73) Assignee: NordicCan A/S ( * ) Notice: Subject to any disclaimer, the term of this patent is extended or adjusted under 35 U.S.C. 154(b) by 0 days.

This patent is subject to a terminal disclaimer.

(21) Appl. No.: 16/257,785

(22) Filed: Jan. 25, 2019

(65) Prior Publication Data
US 2020/0237658 A1 Jul. 30, 2020

(51) Int. Cl.
| A61K 9/68 | (2006.01) |
| A61K 31/05 | (2006.01) |
| A61K 47/69 | (2017.01) |
| A61K 31/352 | (2006.01) |
| A23G 4/08 | (2006.01) |
| A23G 4/06 | (2006.01) |
| A23G 4/12 | (2006.01) |
| A23G 4/10 | (2006.01) |
| A23G 4/18 | (2006.01) |

(52) U.S. Cl.
CPC ............ *A61K 9/0058* (2013.01); *A23G 4/068* (2013.01); *A23G 4/08* (2013.01); *A23G 4/10* (2013.01); *A23G 4/12* (2013.01); *A23G 4/18* (2013.01); *A61K 31/05* (2013.01); *A61K 31/352* (2013.01); *A61K 47/6951* (2017.08); *A23V 2002/00* (2013.01)

(58) Field of Classification Search
None
See application file for complete search history.

(56) References Cited

U.S. PATENT DOCUMENTS

| 6,017,566 | A | 1/2000 | Bunczek et al. |
| 9,023,322 | B2 | 5/2015 | Van Damme et al. |
| 9,433,601 | B2 | 9/2016 | Van Damme et al. |
| 9,744,128 | B2 | 8/2017 | Bachmann et al. |
| 9,833,408 | B1* | 12/2017 | Greenspoon ............ A61K 31/05 |
| 2004/0028772 | A1 | 2/2004 | Andersen |
| 2008/0260899 | A1* | 10/2008 | Schmidt .................... A23G 4/20 426/4 |
| 2009/0298929 | A1 | 12/2009 | Jarho et al. |
| 2012/0288450 | A1* | 11/2012 | Gonzales ............. A61K 36/537 424/48 |
| 2015/0209322 | A1* | 7/2015 | Van Damme ........ A61K 9/0058 424/48 |
| 2016/0220593 | A1* | 8/2016 | Anastassov .......... A61K 31/704 |
| 2016/0354310 | A1 | 12/2016 | Bachmann et al. |
| 2017/0265494 | A1 | 9/2017 | Uccello, III |
| 2017/0273902 | A1 | 9/2017 | Bachmann et al. |
| 2017/0273903 | A1 | 9/2017 | Bachmann et al. |
| 2017/0281539 | A1 | 10/2017 | Bachmann et al. |
| 2017/0312261 | A1 | 11/2017 | Changoer et al. |
| 2017/0368020 | A1 | 12/2017 | Estey et al. |
| 2018/0064645 | A1 | 3/2018 | Greenspoon |
| 2018/0110730 | A1 | 4/2018 | Changoer et al. |
| 2018/0147141 | A1 | 5/2018 | Changoer et al. |
| 2018/0206518 | A1 | 7/2018 | Silver |

FOREIGN PATENT DOCUMENTS

| CA | 2937471 A1 | 9/2016 |
| CA | 2999032 A1 | 3/2017 |
| CA | 2719830 C | 8/2017 |
| CA | 3025559 A1 | 11/2017 |
| CA | 3031530 A1 | 12/2019 |
| EP | 1554935 A1 | 7/2005 |
| WO | 2004004479 A1 | 1/2004 |
| WO | 2006063189 A2 | 6/2006 |
| WO | 2009007769 A1 | 1/2009 |
| WO | 2009080020 A1 | 7/2009 |
| WO | 2009080021 A1 | 7/2009 |
| WO | 2009120080 A1 | 10/2009 |
| WO | 2015154780 A1 | 10/2015 |
| WO | 2016126592 A1 | 8/2016 |
| WO | 2017053731 A1 | 3/2017 |

(Continued)

OTHER PUBLICATIONS

Jette Jacobsen, Lona L. Christrup, and Niels-Henrik Jensen. Medicated Chewing Gum. Am J Drug Deliv 2004; 2 (2): 75-88. (Year: 2004).*

European pharmacopoeia 5.0 Section 2.9.25. Chewing gum, medicated, drug release from downloaded Sep. 29, 2020 from http://library.njucm.edu.cn/yaodian/ep/EP5.0/02_methods_of_analysis/2.9._pharmaceutical_technical_procedures/2.9.25.%20Chewing%20gum,%20medicated,%20drug%20release%20from.pdf(Year: 2005).*

American Dental Association, "Oral Health Topics—Chewing Gum", https://web.archive.org/web/20160915140233/https://www.ada.org/en/member-center/oral-health-topics/chewing-gum, website dated Sep. 15, 2016, downloaded from Internet on Sep. 23, 2019.

(Continued)

*Primary Examiner* — Michael P Cohen
(74) *Attorney, Agent, or Firm* — St. Onge Steward Johnston & Reens LLC

(57) ABSTRACT

A chewing gum for mucosal delivery of cannabinoids, the chewing gum being formulated as an extruded chewing gum including water-soluble chewing gum ingredients mixed into water-insoluble gum base, wherein the gum base includes one or more natural resins in an amount of 10-40% by weight of the gum base, one or more elastomers in an amount of 3-30% by weight of the gum base, and one or more elastomer plasticizers in an amount of 8-50% by weight of the gum base, and wherein the chewing gum includes one or more cannabinoids, and wherein the release rate of the one or more cannabinoids is at least 10% by weight of the one or more cannabinoids within the first 5 minutes upon oral administration.

26 Claims, No Drawings

(56) References Cited

FOREIGN PATENT DOCUMENTS

| WO | 2017059859 A1 | 4/2017 |
| WO | 2017189375 A1 | 11/2017 |
| WO | 2017202424 A1 | 11/2017 |
| WO | 2017223309 A1 | 12/2017 |
| WO | 2018006165 A1 | 1/2018 |
| WO | 2018018152 A1 | 2/2018 |
| WO | 2018075665 A1 | 4/2018 |
| WO | 2018091048 A1 | 5/2018 |

OTHER PUBLICATIONS

Kinghorn, et al. (editors), Phytocannabinoids, vol. 103, Progress in the Chemistry of Organic Natural Products, Chapter 1, "Phytochemistry of *Cannabis sativa* L." written by A. ElSohly, et al., 34 pages, Springer International Publishing, Switzerland, 2017.

Leizer, Cary et al., "The Composition of Hemp Seed Oil and Its Potential as an Important Source of Nutrition", Journal of Nutraceuticals, Functional & Medical Foods, vol. 2(4), pp. 35-53.

International Search Report and Written Opinion of the International Searching Authority Application No. PCT DK2019050305 Completed: Jan. 15, 2020; dated Jan. 31, 2020 13 pages.

International Search Report and Written Opinion of the International Searching Authority Application No. PCT DK2019050306 Completed: Jan. 15, 2020; dated Jan. 31, 2020 12 pages.

International Search Report and Written Opinion of the International Searching Authority Application No. PCT DK2019050308 Completed: Jan. 27, 2020; dated Feb. 3, 2020 11 pages.

International Search Report and Written Opinion of the International Searching Authority Application No. PCT DK2019050309 Completed: Jan. 27, 2020; dated Feb. 3, 2020 11 pages.

International Search Report and Written Opinion of the International Searching Authority Application No. PCT DK2019050303 Completed: Jan. 27, 2020; dated Feb. 3, 2020 12 pages.

International Search Report and Written Opinion of the International Searching Authority Application No. PCT DK2019050304 Completed: Jan. 27, 2020; dated Feb. 3, 2020 11 pages.

International Search Report and Written Opinion of the International Searching Authority Application No. PCT DK2019050302 Completed: Jan. 27, 2020; dated Feb. 3, 2020 12 pages.

International Search Report and Written Opinion of the International Searching Authority Application No. PCT DK2019050307 Completed: Jan. 30, 2020; dated Feb. 12, 2020 13 pages.

International Search Report and Written Opinion of the International Searching Authority Application No. PCT DK2019050310 Completed: Feb. 3, 2020; dated Feb. 12, 2020 13 pages.

International Search Report and Written Opinion of the International Searching Authority Application No. PCT DK2019050311 Completed: Feb. 3, 2020; dated Feb. 12, 2020 13 pages.

\* cited by examiner

CANNABINOID CHEWING GUM WITH IMPROVED RELEASE OF CANNABINOIDS

FIELD OF THE INVENTION

The invention relates to the field of cannabinoids and alleviation or treatment of a condition with one or more cannabinoids. In particular, the invention relates to chewing gum as a vehicle for mucosal delivery of one or more cannabinoids.

BACKGROUND OF THE INVENTION

Cannabinoids are known for their health improving properties and have been used with respect to various medical purposes in the past. Among these medical purposes, cannabinoids have in particular been used for alleviating or treating different kinds of pain and counteracting side effects in relation to cancer treatment, such as nausea.

Traditionally, chewing gum has been described in the prior art as a vehicle for delivery of cannabinoids for alleviation or treatment of medical conditions, such as medical conditions associated with pain. While focus has generally been directed to clinical studies supporting various effects of cannabinoids to the human body, only limited attention is given in the prior art to improving such chewing gum formulations for the purpose of improving release of cannabinoids without addition of components that may interact with sensory properties of the gum.

Since chewing gum is a complex matrix of various types of components which all interact with each other, providing the chewing gum with specified properties, it appears that there is a need in the prior art for improved chewing gum platforms that offer a beneficial release of cannabinoids.

WO 2009/120080 discloses the use of chewing gum as a medical carrier and release vehicle of cannabinoids. The chewing gum disclosed herein may facilitate prolonged release of cannabinoids compared to other types of administering methods. However, various problems and challenges are associated with the chewing gum disclosed, partly based on the specific properties of cannabinoids. While certain specific conventional gum bases are used in formulating the chewing gum disclosed, the gum bases appear to have drawbacks for use in combination with cannabinoids.

In general, less attention is addressed in the prior art to the impact of the gum base and components in the gum base for the release properties of cannabinoids. Also, less attention is given on the impact of the gum base and components in the gum base for the sensory properties of chewing gum with cannabinoids. Here, important sensory properties include initial chew, texture, flavor perception, sweetness perception and off-notes associated with cannabinoids. These properties are both relevant from a convenience perspective in chewing gum, but certainly also in order to support an appropriate delivery of cannabinoids from chewing gum and avoid adverse side effects of cannabinoids.

Hence, there is a need in the prior art for improved chewing gum formulations that solve the above-referenced challenges and problems of the prior art. In particular, there is a need in the prior art for new gum base formulations for use in chewing gum that support appropriate delivery of cannabinoids combined with beneficial sensory properties.

SUMMARY OF THE INVENTION

Accordingly, there is provided a chewing gum for mucosal delivery of cannabinoids, the chewing gum being formulated as an extruded chewing gum comprising water-soluble chewing gum ingredients mixed into water-insoluble gum base, wherein the gum base comprising one or more natural resins in an amount of 10-40% by weight of the gum base, one or more elastomers in an amount of 3-30% by weight of the gum base, and one or more elastomer plasticizers in an amount of 8-50% by weight of the gum base, and wherein the chewing gum comprises one or more cannabinoids, and wherein the release rate of the one or more cannabinoids is at least 10% by weight of the one or more cannabinoids within the first 5 minutes upon oral administration.

The present invention may solve various problems of the prior art and aims at establishing a chewing gum that combines beneficial delivery properties of cannabinoids combined with advantageous sensory properties.

One of the aims of the present invention is to provide a chewing gum formulation that both offers a relatively rapid release of cannabinoids and at the same time possesses beneficial or superior sensory properties. Furthermore, it is contemplated that the present invention may be directed to improvements of the chewing gum vehicle for the purpose of improving release of cannabinoids without addition of components that may interact with sensory properties of the gum.

With respect to release properties, the present invention may offer an improved release profile of cannabinoids compared to conventional gum base. In particular, the specific gum base formulation of the present invention may serve to provide improved release characteristics of cannabinoids compared to conventional gum base applied in combination with cannabinoids.

In the present context, an improved release profile may refer to a higher release of cannabinoids which is particularly seen as an advantage since it has traditionally been a challenge with release of cannabinoids from chewing gum. In order to obtain beneficial health effects both in terms of systemic delivery of cannabinoids as well as local delivery of cannabinoids, it is required that a certain content of cannabinoids are released over time. Hence, rapid release of cannabinoids may be an advantage of the present invention.

In addition, the present invention may serve to provide controlled release of cannabinoids such that the chewing gum is tailored to deliver an effective content of cannabinoids over time and at the same time avoid adverse effects of cannabinoids, such as off-notes. Accordingly, the chewing gum of the present invention may at the same time offer a relatively sustained release of cannabinoids.

The special combination of the present invention with one or more natural resins in a certain amount combined with one or more elastomer plasticizers in a certain amount is particularly advantageous for release characteristics of cannabinoids. It was unexpected to the present inventors that the combination according to the invention would contribute to improved release characteristics of cannabinoids. Importantly, the elastomer plasticizer in the present context serves to plasticize the elastomers present in the gum base. The elastomer plasticizers are not to be considered elastomers by themselves in the present context. The elastomeric properties are provided by the elastomers of the invention, and the elastomer plasticizers are present to plasticize the elastomers in order to obtain the beneficial release characteristics of the present invention.

A very important aspect of the present invention is the provision of beneficial sensory properties. Here, important sensory properties include initial chew, texture, flavor perception, sweetness perception and off-notes associated with cannabinoids. These properties are both relevant from a convenience perspective in chewing gum, but certainly also in order to support an appropriate delivery of cannabinoids from chewing gum, such as an improved release profile, and avoid adverse side effects of cannabinoids.

The present inventors have shown very surprising results with the specific combination of features of the present invention in terms of these sensory properties. It was an unexpected result that the invention could both contribute to an improved release profile, such as rapid release of cannabinoids, and at the same time provide very beneficial sensory properties which in terms may also support an appropriate delivery of cannabinoids from chewing gum and avoid adverse side effects of cannabinoids.

The taste masking challenge is more profound when a higher release of cannabinoids are delivered by such chewing gum. If off-notes are the predominant sensation during administration, convenience may be affected and even more critically, the delivery of cannabinoids may also be affected. Saliva production may be suppressed, and the delivery vehicle may not be handled correctly.

One of the sensory properties that are particularly advantageous is the initial chew. Both in order to secure a desired release of cannabinoids and to improve the sensation by a consumer, it is critical that the initial chew is improved. Also, the texture of the chewing gum during chewing is critical for the release of cannabinoids and the experience as well as convenience during chewing. These properties may be improved by the present invention which was not expected by the inventors of the present invention.

The present gum base may also offer improved taste masking in the sense that the gap between the release of the cannabinoid and the taste masking ingredients may be overall reduced.

Another important result of the specific combination of cannabinoids and gum base composition is that a reduced content of cannabinoids will reduce the requirements for taste masking, or alternatively make the taste masking more efficient. This is important given the fact that when applied as a medical delivery platform, many patients may have difficulties in sensing the taste of cannabinoid.

It should also be noted that this unexpected effect is very attractive in relation to medicated chewing gum in the present context as a large group of the patients who may benefit from the inventive chewing gum will be very vulnerable to off-notes.

In an embodiment of the invention, the release rate of the one or more cannabinoids is at least 15% by weight of the one or more cannabinoids within the first 5 minutes upon oral administration.

In certain embodiments of the invention, the release rate is preferably above 15% within the first 5 minutes after chewing is initiated.

According to the invention, an extruded chewing gum is provided, comprising water-soluble chewing gum ingredients mixed into water-insoluble gum base.

Traditionally, such types of chewing gum has been problematic with cannabinoids due to the fact that release of cannabinoids tends to be low. This is particularly relevant when no release improving agents are added to the extruded chewing gum, which agents may affect the sensory properties of the extruded chewing gum. Also, when agents such a microcrystalline cellulose are added in pre-blends, the sensory properties may be affected.

Since extruded chewing gum is a complex matrix of various types of components which all interact with each other, providing the chewing gum with specified properties, it appears that there is a need in the prior art for improved extruded chewing gum platforms that offer a beneficial release of cannabinoids without compromising sensory properties.

A release rate of more than 15% is considered a relatively rapid release of cannabinoids for extruded chewing gum, while at the same time maintaining beneficial sensory properties.

In some embodiments, the present invention may solve various problems of the prior art and aims at establishing a chewing gum that combines beneficial delivery properties of cannabinoids combined with advantageous sensory properties, such as initial chew, texture, flavor perception, sweetness perception and off-notes associated with cannabinoids. These properties are both relevant from a convenience perspective in chewing gum, but certainly also in order to support an appropriate delivery of cannabinoids from chewing gum and avoid adverse side effects of cannabinoids.

In an embodiment of the invention, the release rate of the one or more cannabinoids is at least 20% by weight of the one or more cannabinoids within the first 5 minutes upon oral administration.

In an embodiment of the invention, the release rate of the one or more cannabinoids is at least 25% by weight of the one or more cannabinoids within the first 5 minutes upon oral administration.

In an embodiment of the invention, the release rate of the one or more cannabinoids is at most 50% by weight of the one or more cannabinoids within the first 5 minutes upon oral administration.

In certain embodiments of the invention, the release rate may be relatively high. This may in particular be the case when cannabinoids are both located in the extruded chewing gum and at the same time in an outer hard coating of the extruded chewing gum. In certain embodiments, this may be the case when cannabinoids are only located in an outer hard coating of the extruded chewing gum.

By locating the cannabinoids in both the extruded chewing gum and in a coating, controlled release of cannabinoids may be possible. Such "bi-phasic" release may be an advantage if for instance the desire is a rapid release from the coating and a more sustained release from the extruded chewing gum over time. In this way, a patient in need thereof may profit from an initial dose of cannabinoids and a more sustained dose of cannabinoids. Combined this may provide a dosage regimen that benefits certain medical treatments.

In some embodiments, the present invention may solve various problems of the prior art and aims at establishing a chewing gum that combines beneficial delivery properties of cannabinoids combined with advantageous sensory properties, such as initial chew, texture, flavor perception, sweetness perception and off-notes associated with cannabinoids. These properties are both relevant from a convenience perspective in chewing gum, but certainly also in order to support an appropriate delivery of cannabinoids from chewing gum and avoid adverse side effects of cannabinoids.

In an embodiment of the invention, the release rate of the one or more cannabinoids is between 10-50% by weight of the one or more cannabinoids within the first 5 minutes upon oral administration.

In certain embodiments of the invention, the release rate may be with the range of 10-50% by weight of the one or more cannabinoids within the first 5 minutes upon oral administration. A content of more than 50% may be critical in some embodiments. This may in particular be relevant when a controlled release is desired. In some circumstances, it is beneficial that the release rate is not too high due to adverse effects, such as off-note problems for a patient under medical treatment with cannabinoids. At the same time, the release rate is at a level where a substantial content of cannabinoids is delivered.

Still, the cannabinoids may both be located in the extruded chewing gum and at the same time in an outer hard coating of the extruded chewing gum. In certain embodiments, this may be the case when cannabinoids are only located in an outer hard coating of the extruded chewing gum.

In some embodiments, the present invention may solve various problems of the prior art and aims at establishing a chewing gum that combines beneficial delivery properties of cannabinoids combined with advantageous sensory properties, such as initial chew, texture, flavor perception, sweetness perception and off-notes associated with cannabinoids. These properties are both relevant from a convenience perspective in chewing gum, but certainly also in order to support an appropriate delivery of cannabinoids from chewing gum and avoid adverse side effects of cannabinoids.

In an embodiment of the invention, the release rate of the one or more cannabinoids is at most 30% by weight of the one or more cannabinoids within the first 5 minutes upon oral administration.

In some circumstances, it is beneficial that the release rate is not too high due to adverse effects, such as off-note problems for a patient under medical treatment with cannabinoids. Still, the cannabinoids may both be located in the extruded chewing gum and at the same time in an outer hard coating of the extruded chewing gum. In certain embodiments, this may be the case when cannabinoids are only located in an outer hard coating of the extruded chewing gum.

In an embodiment of the invention, the release rate of the one or more cannabinoids is between 10-30% by weight of the one or more cannabinoids within the first 5 minutes upon oral administration.

In certain embodiments of the invention, a preferred release rate may be with the range of 10-30% by weight of the one or more cannabinoids within the first 5 minutes upon oral administration. A content of more than 30% is considered to be at an advantageous level.

In an embodiment of the invention, the release rate of the one or more cannabinoids is partly controlled by means of the composition of the water-insoluble gum base.

The special combination of gum base components of the present invention with one or more natural resins in a certain amount combined with one or more elastomer plasticizers in a certain amount is particularly advantageous for release characteristics of cannabinoids. It was unexpected to the present inventors that the combination according to the invention would contribute to improved release characteristics of cannabinoids. Importantly, the elastomer plasticizer in the present context serves to plasticize the elastomers present in the gum base. The elastomer plasticizers are not to be considered elastomers by themselves in the present context. The elastomeric properties are provided by the elastomers of the invention, and the elastomer plasticizers are present to plasticize the elastomers in order to obtain the beneficial release characteristics of the present invention.

In an embodiment of the invention, the release rate of the one or more cannabinoids is partly controlled by means of the amount of the one or more natural resins.

The natural resins provide beneficial properties to the present invention. In particular the combination of natural resins and elastomer plasticizers provides beneficial properties to the gum base and followingly to the chewing gum formulation in general, both in terms of release properties of cannabinoids and sensory properties.

In an embodiment of the invention, the release rate of the one or more cannabinoids is partly controlled by means of the amount of the one or more elastomer plasticizers.

The elastomer plasticizers provide beneficial properties to the present invention. In particular the combination of natural resins and elastomer plasticizers provides beneficial properties to the gum base and followingly to the chewing gum formulation in general, both in terms of release properties of cannabinoids and sensory properties.

In an embodiment of the invention, the release rate of the one or more cannabinoids is partly controlled by means of the water-soluble chewing gum ingredients.

The water-soluble ingredients provide beneficial properties to the present invention. In particular, when water-soluble chewing gum ingredients are combined with natural resins and elastomer plasticizers of the present invention, beneficial properties to the gum base applies, both in terms of release properties of cannabinoids and sensory properties.

In an embodiment of the invention, the release rate of the one or more cannabinoids are partly controlled by means of the location of the one or more cannabinoids in the chewing gum.

In an embodiment of the invention, the one or more cannabinoids are comprised in an outer coating of the extruded chewing gum.

In certain embodiments of the invention, cannabinoids are located in an outer hard coating of the extruded chewing gum, such as an outer hard coating of the extruded chewing gum. In certain embodiments, cannabinoids are only located in the coating and not in the extruded chewing gum matrix.

By locating the cannabinoids in an outer coating, more rapid release of cannabinoids may be possible. In this way, a patient in need thereof may profit from an initial high dose of cannabinoids in a dosage regimen that benefits certain medical treatments.

In an embodiment of the invention, the one or more cannabinoids are comprised in the extruded chewing gum.

In certain embodiments of the invention, cannabinoids are located in the extruded chewing gum. In certain embodiments, cannabinoids are only located in the extruded chewing gum and not in a coating of the extruded chewing gum matrix.

By locating the cannabinoids in the extruded chewing gum, a more sustained release of cannabinoids may be possible. In this way, a patient in need thereof may profit from an initial high dose of cannabinoids in a dosage regimen that benefits certain medical treatments.

In an embodiment of the invention, the one or more cannabinoids are both comprised in the extruded chewing gum and an outer coating of the extruded chewing gum.

In certain embodiments of the invention, the release rate may be relatively high. This may in particular be the case when cannabinoids are both located in the extruded chewing gum and at the same time in an outer hard coating of the extruded chewing gum. In certain embodiments, this may be the case when cannabinoids are only located in an outer hard coating of the extruded chewing gum.

By locating the cannabinoids in both the extruded chewing gum and in a coating, controlled release of cannabinoids may be possible. Such "bi-phasic" release may be an advantage if for instance the desire is a rapid release from the coating and a more sustained release from the extruded chewing gum over time. In this way, a patient in need thereof may profit from an initial dose of cannabinoids and a more sustained dose of cannabinoids. Combined this may provide a dosage regimen that benefits certain medical treatments.

In an embodiment of the invention, the release rate of the one or more cannabinoids is partly controlled by means of further release enhancing ingredients.

In an embodiment of the invention, the one or more cannabinoids are comprised in the water-soluble chewing gum ingredients mixed into water-insoluble gum base.

In an embodiment of the invention, the one or more cannabinoids are homogeneously distributed in the water-insoluble gum base.

By distributing the one or more cannabinoids homogeneously in the water-insoluble gum base, it may be secured that maximal effect is achieved with respect to release of the cannabinoids. Furthermore, it would not have been expected that cannabinoids in close association with the water-insoluble gum base would release to the degree as seen by the inventors of the present invention.

Traditionally, water-insoluble gum base is seen as a matrix that does not offer a high degree of release of cannabinoids. In particular, with respect to cannabinoids, it is a surprise that improved release may be seen.

In an embodiment of the invention, the one or more cannabinoids are mixed into the water-insoluble gum base in unbound form.

A particular advantage is seen when the cannabinoids are present in unbound form. In general, the cannabinoids are present in unbound form. By "unbound form" is meant that the cannabinoids are not bound to any carrier material that limits free transfer and release of the cannabinoids in the chewing gum formulation. An example of "bound form" is if the cannabinoids are part of a plant material and the cannabinoids are not extracted and separated from the plant material. Other examples may be a pre-blend of microcrystalline cellulose which was seen by the inventors to limit free transfer of cannabinoids in the chewing gum formulation. Also, in some embodiments, other pre-blends with water-insoluble carrier is to be avoided due to both problems with sensation appearance and release of cannabinoids.

The advantage of having the cannabinoids in free form may also be improved sensory characteristics. For instance, plant material may compromise the chewing gum matrix and for instance microcrystalline cellulose may impact the texture of the chewing gum and the complex matrix of chewing gum in general.

In an embodiment of the invention, at least 10% by weight of the one or more cannabinoids are present in unbound form.

Within the limits of the present invention, a certain content of cannabinoids may be present in bound form as long as a certain amount will also be present in unbound form.

In an embodiment of the invention, at least 90% by weight of the one or more cannabinoids are present in unbound form.

The advantage of having the cannabinoids in free form may also be improved sensory characteristics. For instance, plant material may compromise the chewing gum matrix and for instance microcrystalline cellulose may impact the texture of the chewing gum and the complex matrix of chewing gum in general.

In an embodiment of the invention, the one or more elastomer plasticizers are present in an amount of 15-35% by weight of the gum base.

A particularly preferred range of elastomer plasticizers, such as polyvinyl acetate elastomer plasticizers, is 15-35% by weight of the gum base. Here, very advantageous results were achieved with respect to release of cannabinoids and sensory characteristics, such as initial chew, texture, flavor perception, sweetness and off-notes. That the preferred range would be on a level such high was a surprise to the inventors. Also, it was not expected that such high amount of elastomer plasticizers, such as polyvinyl acetate elastomer plasticizers, would have a combined effect of improved sensory properties.

In other embodiments of the invention, the one or more elastomer plasticizers, such as polyvinyl acetate elastomer plasticizers, are present in an amount of 17-33% by weight of the gum base. In other embodiments of the invention, the one or more elastomer plasticizers, such as polyvinyl acetate elastomer plasticizers, are present in an amount of 20-35% by weight of the gum base. In other embodiments of the invention, the one or more elastomer plasticizers, such as polyvinyl acetate elastomer plasticizers, are present in an amount of 20-30% by weight of the gum base. In other embodiments of the invention, the one or more elastomer plasticizers, such as polyvinyl acetate elastomer plasticizers, are present in an amount of 15-40% by weight of the gum base. In other embodiments of the invention, the one or more elastomer plasticizers, such as polyvinyl acetate elastomer plasticizers, are present in an amount of 20-40% by weight of the gum base.

In an embodiment of the invention, the gum base comprises less than 50% by weight of gum base polymers.

In order to achieve the effects of the invention, it may in some embodiments be preferred that the content of polymers is relatively low. This ensures for instance that the release of cannabinoids may be improved and that the sensory properties of the chewing gum may be improved. In particular, when vinyl laurate-vinyl acetate copolymer are applied, it appears critical that the content of gum base polymers should be below 50% by weight of the gum base. It appears that this polymer may compromise the chewing gum formulation in the present context.

In an embodiment of the invention, the gum base does not comprise vinyl laurate-vinyl acetate copolymer.

To the surprise of the inventors, it was seen that vinyl laurate-vinyl acetate copolymer may compromise the release of cannabinoids and the sensory characteristics of the chewing gum. Hence, it is preferred that this copolymer is not present in the gum base.

In certain other embodiments, the gum base polymers comprise less than 20% by weight of vinyl laurate-vinyl acetate copolymer. In certain other embodiments, the gum base polymers comprise less than 15% by weight of vinyl laurate-vinyl acetate copolymer. In certain other embodiments, the gum base polymers comprise less than 10% by weight of vinyl laurate-vinyl acetate copolymer. In certain other embodiments, the gum base polymers comprise less than 5% by weight of vinyl laurate-vinyl acetate copolymer.

In some embodiments of the invention, if polyvinyl acetate elastomers are present in the gum base formulation, the gum base polymers comprise less than 20% by weight of vinyl laurate-vinyl acetate copolymer, such as less than 10%, such as less than 5%. In the present context, polyvinyl acetate elastomers are not the same as polyvinyl acetate elastomer plasticizers. Basically, polyvinyl acetate elastomers provides elastomeric properties to the chewing gum, whereas polyvinyl acetate elastomer plasticizers work to plasticize the elastomers present in the gum base.

In an embodiment of the invention, the one or more natural resins are present in an amount of 15-35% by weight of the gum base.

The natural resins provides beneficial properties to the present invention. In particular the combination of natural resins and elastomer plasticizers provides beneficial properties to the gum base and followingly to the chewing gum formulation in general, both in terms of release properties of cannabinoids and sensory properties.

A particularly advantageous range of natural resins is 15-35% by weight of the gum base. This range of natural resin was seen to give an improved release profile and best sensory properties. While natural resins of 10-40% by weight of gum base is also within the scope of the invention, the best results were seen with 15-35% by weight of the gum base.

In other embodiments of the invention, the one or more natural resins are present in an amount of 17-33% by weight of the gum base. In other embodiments of the invention, the one or more natural resins are present in an amount of 20-35% by weight of the gum base. In other embodiments of the invention, the one or more natural resins are present in an amount of 20-30% by weight of the gum base. In other embodiments of the invention, the one or more natural resins are present in an amount of 15-40% by weight of the gum base. In other embodiments of the invention, the one or more natural resins are present in an amount of 20-40% by weight of the gum base.

In an embodiment of the invention, the one or more natural resins are selected from the group consisting of polyterpene resins, resins based on gum rosin, wood rosin or tall oil resin.

In an embodiment of the invention, the one or more elastomers are selected from the group consisting of styrene-butadiene copolymers, polyisobutylene, isobutylene-isoprene copolymers, polyethylene, polyurethane or any combination thereof.

In an embodiment of the invention, the one or more elastomers are present in an amount of 3-20% by weight, such as in an amount of 3-15% by weight, such as in an amount of 5-10% by weight.

In an embodiment of the invention, the chewing gum comprises water-soluble chewing gum ingredients in an amount of 40-70% by weight of the chewing gum.

It is particularly preferred that the water-soluble chewing gum ingredients are present in an amount of 40-70% by weight of the chewing gum. This range of water-soluble chewing gum ingredients have shown particularly beneficial results. The inventors of the present invention did not expect that an improved release would be possible within this range of water-soluble chewing gum ingredients. As the water-soluble chewing gum ingredients are mixed into the gum base during the manufacturing process, it was expected the water-soluble ingredients did not provide enough porosity of the chewing gum to facilitate an improved release. In addition, due to the specific properties of cannabinoids, it was a surprise to discover that the release rate of cannabinoids was improved with water-soluble chewing gum ingredients.

Importantly, the sensory characteristics were thought to be compromised when the water-soluble chewing gum ingredients are present in an amount of 40-70% by weight of the chewing gum. However, contrary to expectations, the sensory properties were improved in combination with an improved release of cannabinoids. In particular, the texture of the chewing gum was improved. It was expected that the texture would be worse with this amount of water-soluble ingredients in the chewing gum.

In an embodiment of the invention, the water-soluble chewing gum ingredients comprise at least one sugar alcohol.

Best results were seen when the water-soluble chewing gum ingredients comprised at least one sugar alcohol. Both with respect to release properties and sensory properties, the chewing gum was improved when at least one sugar alcohol was present in the formulation.

In an embodiment of the invention, the water-soluble chewing gum ingredients comprise at least one saccharose.

In an embodiment of the invention, the one or more cannabinoids are mixed into the water-insoluble gum base as part of a pre-mixture with water-soluble chewing gum ingredients.

This aspect of the invention was particularly surprising since it was not expected that the time of adding sugar alcohols would have in impact of the properties of the finished chewing gum. However, both the release rate and sensory properties were improved by adding the sugar alcohol in the manufacturing process after more than half the mixing time. This was highly significant.

In the present context, a premixture is mainly used to allocate the one or more cannabinoids properly to the manufacturing process and secure that the uniformity is not compromised and that the cannabinoids are distributed properly into the mixture.

Preferably, the cannabinoids are provided in a premixture with one or more sugar alcohols. It was a surprise to the inventors that a premixture was important to have the cannabinoids distributed properly in the manufacturing process and to end up with a product where the uniformity was consistent.

In an embodiment of the invention, the one or more cannabinoids are not part of a pre-mixture with microcrystalline cellulose.

In certain embodiments of the invention, the cannabinoids are not part of a pre-mixture with microcrystalline cellulose. It was seen that both release rate of cannabinoids and sensory properties were to some degree compromised by using microcrystalline cellulose in premixture. Without being bound by theory, it is expected that cannabinoids are bound to a higher degree to microcrystalline cellulose than preferred.

In some embodiments, less than 50% of the cannabinoids are part of a pre-mixture with microcrystalline cellulose. In some embodiments, less than 20% of the cannabinoids are part of a pre-mixture with microcrystalline cellulose. In some embodiments, less than 10% of the cannabinoids are part of a pre-mixture with microcrystalline cellulose.

In an embodiment of the invention, the one or more cannabinoids are present in an amount of 0.1 to 200 mg. In some other embodiments of the invention, the one or more cannabinoids are present in an amount of 0.1 to 100 mg. In some other embodiments of the invention, the one or more cannabinoids are present in an amount of 0.1 to 50 mg. In an embodiment of the invention said chewing gum comprises said cannabinoids in an amount of 0.1-30 mg, such as 1-20 mg, such as 5-15 mg.

In an embodiment of the invention, the one or more cannabinoids comprise cannabidiol (CBD), cannabidiolic acid (CBDA), cannabidivarin (CBDV), salts and derivatives thereof. In an embodiment of the invention the one or more cannabinoids comprises CBD, salts and derivatives thereof, including analogues and homologues. In an embodiment of the invention said one or more cannabinoids comprises cannabidiol (CBD). In an embodiment of the invention said one or more cannabinoids is CBD.

In an embodiment of the invention, the one or more cannabinoids comprise tetrahydrocannabinol (THC), tetrahydrocannabinolic acid (THCA), tetrahydrocannabivarin (THCV), salts and derivatives thereof. In an embodiment of the invention said one or more cannabinoids comprises tetrahydrocannabinol (THC). Preferably THC is intended to mean (−)-trans-$\Delta^9$-tetrahydrocannabinol, i.e. (6aR,10aR)-delta-9-tetrahydrocannabinol). In an embodiment of the invention said one or more cannabinoids is THC.

In an embodiment of the invention, the one or more cannabinoids comprise cannabigerol (CBG), salts and derivatives thereof.

In an embodiment of the invention, the one or more cannabinoids comprise at least two cannabinoids. In an embodiment of the invention said one or more cannabinoids comprises a combination of several cannabinoids, such as THC and CBD. In an embodiment of the invention said one or more cannabinoids is a combination of THC and CBD.

In an embodiment of the invention the chewing gum comprises gum base in an amount of 30-75% by weight of the chewing gum before any optionally applied coating, such as 35-70% by weight of the chewing gum or 40-65% by weight of the chewing gum or 45-60% by weight of the chewing gum.

In an embodiment of the invention the chewing gum comprises wax. In an embodiment of the invention the chewing gum comprises fat.

In an embodiment of the invention the chewing gum comprises flavor in an amount between 0.01 and 10% by weight of the chewing gum such as in an amount between 0.01 and 5% by weight of the chewing gum.

According to an advantageous embodiment of the invention, the chewing gum may be formulated with flavors, e.g. flavors including acids, which may be more acceptable for seriously ill patients, such as patients receiving chemotherapy.

In an embodiment of the invention the chewing gum comprises high intensity sweetener.

In an embodiment of the invention the chewing gum is manufactured in a two-step process, the first step including the process of providing gum base in a first mixing process and a further step including the process of mixing gum base with further chewing gum components in a further mixing process. In an embodiment of the invention the chewing gum is manufactured in a one step process by means of an extruder. This is referred to as extruded chewing gum.

In an embodiment of the invention, the one or more cannabinoids are present in solid form. In an embodiment of the invention, the one or more cannabinoids are present in liquid or semi-liquid form. In an embodiment of the invention, the one or more cannabinoids are present in granules.

In an embodiment of the invention, the one or more cannabinoids are present in a pre-mixture with one or more sugar alcohols or saccharose.

In the present context, a pre-mixture is mainly used to allocate the one or more cannabinoids properly to the manufacturing process and secure that the uniformity is not compromised and that the cannabinoids are distributed properly into the mixture. Preferably, the cannabinoids are provided in a premixture with one or more sugar alcohols. It was a surprise to the inventors that a premixture was important to have the cannabinoids distributed properly in the manufacturing process and to end up with a product where the uniformity was consistent.

In an embodiment of the invention, the chewing gum comprises further release enhancing ingredients.

In an embodiment of the invention, the one or more cannabinoids form part of a complex with cyclodextrin. This complex may enhance the release of cannabinoids according to the present invention.

In an embodiment of the invention, the one or more cannabinoids comprise at least one phytocannabinoid that forms part of an extract. In some embodiments of the invention, it was seen that cannabinoids as part of an extract may enhance the release of cannabinoids. It was also seen that the lower concentration applied in the extract, the higher release.

In an embodiment of the invention, the chewing gum further comprising terpenes, such as at least one terpene that forms part of an extract.

In an embodiment of the invention, the one or more cannabinoids comprise at least one isolated cannabinoid.

In an embodiment of the invention, the one or more cannabinoids comprise at least one water-soluble cannabinoid. Water-soluble cannabinoids may enhance the release according to the present invention.

In an embodiment of the invention, the chewing gum comprises one or more emulsifiers.

In an embodiment of the invention the chewing gum comprises emulsifiers in an amount of 0.1% to 25% by weight of said chewing gum, such as 1-10% by weight of said chewing gum, such as 2-8% by weight of said chewing gum.

In an embodiment of the invention the emulsifiers are selected from the group of acetylated monoglycerides, mono- and/or di-glycerides of fatty acids such as glycerol monostearate, acetem, lecithin and any combination thereof.

In an embodiment of the invention, the chewing gum comprises one or more solubilizers.

In an embodiment of the invention, the chewing gum comprises a self-emulsifying agent.

In an embodiment of the invention, the chewing gum comprises a polymer carrier for the one or more cannabinoids.

In an embodiment of the invention, the chewing gum comprises a lipid carrier for the one or more cannabinoids.

In an embodiment of the invention, the chewing gum comprises enzyme inhibitors.

In an embodiment of the invention, the chewing gum comprises one or more antioxidants.

In an embodiment of the invention, the one or more cannabinoids have a systemic effect.

In an embodiment of the invention, the one or more cannabinoids have a local effect.

In an embodiment of the invention, the one or more cannabinoids are comprised in an outer coating of the chewing gum.

In certain embodiments of the invention, the cannabinoids are present in the coating of the chewing gum. This is particularly preferred when an enhanced release of cannabinoids are preferred. Also, if controlled release of cannabinoids is preferred, it is an advantage to allocate cannabinoids in the coating. It was not expected by the inventors of the present invention that it was possible to use a coating to deliver cannabinoids. By combining cannabinoids in the coating and in the chewing gum, controlled release of cannabinoids may be provided. In the present context, cannabinoids may both be allocated in the coating, in the chewing gum or in both places.

In an embodiment of the invention, the one or more cannabinoids are comprised in an outer soft coating of the chewing gum. In certain embodiments, this coating is a film coating.

In another aspect of the invention, the chewing gum of the present invention may be used for the treatment or alleviation of a medical condition.

In certain embodiments of the invention, the chewing gum of the present invention may be used for the treatment or alleviation of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In the present context, the chewing gum of the invention may be applied for the medical indications as single indications from the list of indications. The invention may also be applied for other medical indications and indications that are not medical for instance local conditions in the mouth, such as bacterial infections or gingivitis, that may be treated or alleviated with the formulation of the present invention. The list is not exhaustive and other indications are part of the present invention.

In another aspect of the invention, a package is provided comprising a chewing gum according to the invention, the package comprising a material acting as a barrier for the one or more cannabinoids and oxygen, preferably a copolymer of acrylonitrile and methyl acrylate.

In certain embodiments of the invention, the package comprising a chewing gum according to the invention, wherein the package includes a liquid or a semisolid for the provision of a preventive environment therein.

In certain embodiments of the invention, the package comprising a chewing gum according to the invention, wherein the package is a blister package.

In another aspect of the invention, there is provided a method of producing extruded chewing gum for increased release of one or more cannabinoids, the method comprising the steps of:
i) providing water-insoluble gum base, water-soluble chewing gum ingredients and one or more cannabinoids,
ii) mixing a first amount of water-soluble chewing gum ingredients into the water-insoluble gum base under elevated temperature to obtain a mixture of gum base and water-soluble chewing gum ingredients,
iii) mixing a second amount of water-soluble chewing gum ingredients into the mixture after a period of time,
iv) dosing the one or more cannabinoids to the mixture after a period of time, and
v) extruding the final composition to obtain a chewing gum.

In certain embodiments of the method, the gum base comprising one or more natural resins in an amount of 10-40% by weight of the gum base, one or more elastomers in an amount of 3-30% by weight of the gum base, and one or more elastomer plasticizers in an amount of 8-50% by weight of the gum base.

In certain embodiments of the method, the one or more elastomer plasticizers comprise one or more polyvinyl acetate elastomer plasticizers, and the one or more polyvinyl acetate elastomer plasticizers are present in an amount of 8-50% by weight of the gum base.

In certain embodiments of the method, the first amount of water-soluble chewing gum ingredients comprise one or more sugar alcohols.

In certain embodiments of the method, the second amount of water-soluble chewing gum ingredients comprise one or more sugar alcohols.

In certain embodiments of the method, the one or more cannabinoids are mixed into the mixture at about the same time as mixing the second amount of water-soluble chewing gum ingredients into the mixture.

In certain embodiments of the method, the one or more cannabinoids are mixed into the mixture after a period of time of more than half the total mixing time.

In certain embodiments of the method, the one or more cannabinoids are mixed into the mixture as close as possible to the end of mixing while at the same time securing that the one or more cannabinoids are homogeneously distributed in the water-insoluble gum base comprising the one or more polyvinyl acetate elastomer plasticizers.

In certain embodiments of the method, the one or more cannabinoids are included in a pre-mixture prior to mixing, the pre-mixture comprising one or more sugar alcohols.

In certain embodiments of the method, the method comprises a step v) of adding an outer coating to the chewing gum.

In certain embodiments of the method, the one or more cannabinoids are comprised in the outer coating of the chewing gum.

In certain embodiments of the method, high intensity sweeteners are mixed into the water-insoluble gum base.

In certain embodiments of the method, flavors are mixed into the water-insoluble gum base.

In certain embodiments of the method and product, the water-insoluble gum base is a natural gum base comprising natural ingredients, such as chicle.

In certain embodiments of the method, the chewing gum is formulated according to any of the product embodiments of the invention.

DETAILED DESCRIPTION OF THE INVENTION

The invention will now be described in more details with respect to certain aspects and embodiments of the invention. These aspects and embodiments are intended to be understood in connection with the rest of the description, including the Summary of the Invention and Examples of the invention.

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in concert with the word comprising or containing denote "one or more."

By the terms "gum base" and "gum base matrix" is meant the mainly water-insoluble ingredients and hydrophobic gum base ingredients that are mixed together, typically before the bulk portion of the chewing gum is added. The "gum base" may contain gum base polymers and plasticizers, waxes, emulsifiers, fats and/or fillers. The gum base may thus designate the typical water-insoluble chewing gum components, which may be manufactured in a first step and subsequently mixed with the mainly water soluble portion in a second step. The term gum base may, evidently, also refer to the relevant gum base components that may be fed into an extruder and forming part of the final chewing gum when mixed with the chewing gum components in the extruder.

The term "bulk portion" or "water-soluble ingredients" intends to mean the mainly water-soluble and hydrophilic chewing gum ingredients that may be mixed into the gum base matrix, either in a separate process or in a one-step process by means of an extruder.

The term "weight of the chewing gum" or similar wording meaning the same is defined in the present context as weight of the chewing gum, not including the weight of an outer coating, such as a hard coating, soft coating, and the like.

By the phrase "texture" is meant a qualitative measure of the viscoelastic properties of the chewing gum and of the overall mouth-feel experienced by the user during the chewing process. Thus, the term "texture" encompasses measurable quantities such as hardness and elasticity as well as more subjective parameters related to the chew-feel experienced by a user.

The term "in vivo chewing" intends to mean that the chewing gum system is chewed by a human subject in an experimental setup of trained test persons according to statistically principles and that either the saliva of the human subject is subject to measurements or the chewed chewing gum is subject to measurements, the experimental setup being performed at a chewing frequency of 60 chews per minute.

The term "in vivo release" or "in vivo testing of release" or similar wording intends to mean that the chewing gum is tested according to Example 24.

The term "in vitro release" or "in vitro testing of release" or similar wording intends to mean that the chewing gum is tested according to Example 25, in particular according to Dissolution Test for Chewing Gums, General Monograph 2.9.25. In European Pharmacopoeia, 5th ed.

The term "release" in the present context is intended to mean under "in vivo" or "in vitro" conditions. In particular, the "release rate" during a certain period of time is intended to mean the amount in percentage of cannabinoids that is released during the period at a chewing frequency of 60 chews per minute.

The term "sustained release" or "extended release" is herein intended to mean prolonged release over time. The term "rapid release" or "quick release" or "high release" is herein intended to mean a higher content released for a given period of time. The term "controlled release" is intended to mean a release of a substance from a gum by the aid of active chewing of the gum in the oral cavity of the subject, whereby the active chewing is controlling the amount of substance released.

The term "delivery to the oral mucosa" or similar wording intends to mean that the chewing gum is tested according to Example 27.

A "self-emulsifying agent" is an agent which will form an emulsion when presented with an alternate phase with a minimum energy requirement. In contrast, an emulsifying agent, as opposed to a self-emulsifying agent, is one requiring additional energy to form an emulsion.

The term "natural resin", as used herein, means resinous compounds being either polyterpene derived from terpenes of natural origin or resinous compounds derived from gum rosin, wood rosin or tall-oil rosin.

The gum base is the masticatory substance of the chewing gum, which imparts the chew characteristics to the final product. The gum base typically defines the release profile and plays a significant role in the gum product. The gum base portion is retained in the mouth throughout the chew. The water-soluble portion disappears over a period of time during chewing.

According to embodiments of the invention, a preferred amount of gum base matrix in the final chewing gum is 30-75% by weight of the chewing gum before any optionally applied coating, such as 35-70% by weight of the chewing gum or 40-65% by weight of the chewing gum or 45-60% by weight of the chewing gum.

Elastomers provide the rubbery, elastomeric and bouncing nature to the gum, which varies depending on this ingredient's chemical structure and how it may be compounded with other ingredients. Elastomers suitable for use in the gum base and gum of the present invention may include natural or synthetic types. Polyvinyl acetate elastomer plasticizers are not considered elastomers according to the invention.

Elastomers may be selected from the group consisting of styrene-butadiene copolymers, polyisobutylene, isobutylene-isoprene copolymers, polyethylene, polyurethane or any combination thereof. Preferred elastomers are styrene-butadiene copolymers (SBR), polyisobutylene and isobutylene-isoprene copolymers (BR).

Butadiene-styrene type elastomers, or SBR as they may be called, typically are copolymers of from about 20:80 to 60:40 styrenes:butadiene monomers. The ratio of these monomers affects the elasticity of the SBR as evaluated by mooney viscosity. As the styrene:butadiene ratio decreases, the mooney viscosity decreases.

The structure of SBR typically consists of straight chain 1,3-butadiene copolymerized with phenylethylene (styrene). The average molecular weight of SBR is <600.000 g/mole.

Isobutylene-isoprene type elastomers, or butyl as they may be called, have molar percent levels of isoprene ranging from 0.2 to 4.0. Similar to SBR, as the isoprene:isobutylene ratio decreases, so does the elasticity, measured by mooney viscosity.

The structure of butyl rubber typically consists of branched 2-methyl-1,3-butadiene (isoprene) copolymerized with branched 2-methylpropene (isobutylene). The average molecular weight of SBR is in the range from 150.000 g/mole to 1.000.000 g/mole.

Polyisobutylene, or PIB as they may be called, type elastomers are polymers of 2-methylpropeneThe low molecular weight elastomers provide soft chew characteristics to the gum base and still provide the elastic qualities as do the other elastomers. Average molecular weights may range from about 30,000 to 120,000 g/mole and the penetration may range from about 4 millimeters to 20 millimeters. The higher the penetration, the softer the PIB. Similar to the SBR and butyl, the high molecular weight elastomers provide elasticity the gum. Average molecular weight may range from 120.000 to 1.000.000 g/mole.

Polybutene range in average molecular weight from about 5.000 g/mole to about 30.000 g/mole.

Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang. Natural elastomers may also be applied in aspects of the present invention.

Elastomer plasticizers vary the firmness of the gum base. Their specificity on elastomer inter-molecular chain breaking (plasticizing) along with their varying softening points cause varying degrees of finished gum firmness and compatibility when used in base. Polyvinyl acetate elastomers plasticizers are examples of elastomer plasticizers of the present invention.

In some embodiments of the invention, the weight-average molecular weight (Mw) of the one or more polyvinyl acetate elastomer plasticizers is from 5,000 to 40,000. In some embodiments of the invention, the weight-average molecular weight (Mw) of the one or more polyvinyl acetate elastomer plasticizers is from 6,000 to 35,000. In some embodiments of the invention, the weight-average molecular weight (Mw) of the one or more polyvinyl acetate elastomer plasticizers is from 7,000 to 30,000. In some embodiments of the invention, the weight-average molecular weight (Mw) of the one or more polyvinyl acetate elastomer plasticizers is from 8,000 to 25,000. In some embodiments of the invention, the weight-average molecular weight (Mw) of the one or more polyvinyl acetate elastomer plasticizers is from 10,000 to 20,000.

In some embodiments of the invention, the viscosity of the one or more polyvinyl acetate elastomer plasticizers is from 1.0 to 3.0 mPa*s as measured according to ASTM D445-06 (10 wt. % in ethyl acetate), such as from 1.0 to 2.5 mPa*s.

In some embodiments of the invention, the K value of the one or more polyvinyl acetate elastomer plasticizers is from 15 to 33 as measured according to DIN 53726 (1 wt. % in acetone), such as from 18 to 30.

Generally, the term "polyvinyl acetate elastomer plasticizer" is intended to mean polyvinyl acetate having a weight-average molecular weight (Mw) of less than about 40,000.

Generally, the term "polyvinyl acetate elastomer" is intended to mean polyvinyl acetate having a weight-average molecular weight (Mw) of more than about 40,000.

In certain embodiments of the invention, the gum base comprises less than 10% by weight of polyvinyl acetate elastomer. In certain embodiments of the invention, the gum base comprises less than 5% by weight of polyvinyl acetate elastomer. In certain embodiments of the invention, the gum base comprises 2 to 6% by weight of polyvinyl acetate elastomer. In certain embodiments of the invention, the gum base comprises 3 to 5% by weight of polyvinyl acetate elastomer. In certain embodiments of the invention, the gum base is substantially free of polyvinyl acetate elastomer In certain embodiments of the invention, the gum base comprises 15-35% by weight of the one or more polyvinyl acetate elastomer plasticizers and less than 10% by weight of polyvinyl acetate elastomer. In certain embodiments of the invention, the gum base comprises 15-35% by weight of the one or more polyvinyl acetate elastomer plasticizers and less than 5% by weight of polyvinyl acetate elastomer. In certain embodiments of the invention, the gum base comprises 15-35% by weight of the one or more polyvinyl acetate elastomer plasticizers and 2 to 6% by weight of polyvinyl acetate elastomer.

Natural resins may be selected from ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the chewing gum comprises further chewing gum ingredients selected from the group consisting of flavors, dry-binders, tableting aids, anti-caking agents, emulsifiers, antioxidants, enhancers, absorption enhancers, high intensity sweeteners, softeners, colors, active ingredients, water-soluble indigestible polysaccharides, water-insoluble polysaccharides or any combination thereof.

According to embodiments of the invention, the emulsifiers may be selected from the group consisting of sucrose ester of fatty acids (such as sucrose mono stearate), polyethylene glycol esters or ethers (PEG) (such as caprylocaproyl macrogol-8 glycerides and lauroyl macrogol-32-glycerides), mono- and diglyceride of fatty acids (such as glycerol monostearate, glycerol monolaurate, glyceryl behenate ester), acetic acid esters of mono- and diglycerides of fatty acids (Acetem), polyoxyethylene alkyl ethers, diacetyl tartaric ester of monoglycerides, lactylated monoglycerides, glycerophospholipids (such as lecithin), poloxamer (non-ionic block copolymer of ethylene oxide and propylene oxide), cyclodextrins, fatty acid esters of sorbitol (such as sorbitan monolaurate, sorbitan monostearate, sorbitan tristearate, polysorbates). Self-emulsifying emulsifiers may be phospholipids (Lecithin), Polysorbates (polysorbate 80).

SEDDS (self-emulsifying drug delivery system) may consist of hard or soft capsules filled with a liquid or a gel that consists of self-emulsifiers, one or more cannabinoids, oil (to dissolve the cannabinoids) and a surfactant. SEDDS may comprise of a blend or mixture of self-emulsifiers, one or more cannabinoids, oil (to dissolve the cannabinoids) and a surfactant. SEDDS may comprise granules comprising self-emulsifiers, one or more cannabinoids, oil (to dissolve the cannabinoids) and a surfactant. Upon contact with gastric fluid, the SEDDS spontaneously emulsify due to the presence of surfactants. Many surfactants, however, are lipid based and interact with lipases in the GIT (gastro intestinal tract). This can lead to a reduced capability of the lipid-based surfactants to emulsify the one or more cannabinoids as well as the oil carrier, both reducing bioavailability.

According to embodiments of the invention, flavors may be selected from the group consisting of coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C (ascorbic acid or corresponding salts (ascorbates)), propyl gallate, catechins, other synthetic and natural types or mixtures thereof.

Further chewing gum ingredients, which may be included in the chewing gum according to the present invention, include surfactants and/or solubilizers. As examples of types of surfactants to be used as solubilizers in a chewing gum composition according to the invention, reference is made to H.P. Fiedler, Lexikon der Hilfstoffe für Pharmacie, Kosmetik and Angrenzende Gebiete, pages 63-64 (1981) and the lists of approved food emulsifiers of the individual countries. Anionic, cationic, amphoteric or non-ionic solubilizers can be used. Suitable solubilizers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilizers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, block-copolymers of ethylene oxide and propyleneoxide and polyoxyethylene fatty alcohol ether. The solubilizer may either be a single compound or a combination of several compounds. In the presence of an active ingredient, such as the included one or more cannabinoids, the chewing gum may preferably also comprise a carrier known in the arts of chewing gum and active ingredients. Poloxamer F68 is a further highly suitable solubilizer.

High intensity artificial sweetening agents can also be used according to preferred embodiments of the invention. Preferred high intensity sweeteners include, but are not limited to sucralose, aspartame, salts of acesulfame, alitame, neotame, saccharin and its salts, cyclamic acid and its salts, glycyrrhizin, dihydrochalcones, thaumatin, monellin, monk fruit extract, advantame, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the high-intensity sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated high-intensity sweetener will be proportionately higher.

A chewing gum and/or gum base may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof. According to an embodiment of the invention, one preferred filler/texturizer is calcium carbonate.

A number of chewing gum components well known within the art may be applied within the scope of the present invention. Such components comprise but are not limited to waxes, fats, softeners, fillers, bulk sweeteners, flavors, antioxidants, emulsifiers, coloring agents, binding agents and acidulants.

In an embodiment of the invention, water-soluble ingredients comprise at least one sugar alcohol. The at least one sugar alcohol may be selected from the group consisting of xylitol, sorbitol, mannitol, maltitol, isomaltitol, isomalt, erythritol, lactitol, maltodextrin, hydrogenated starch hydrolysates, and combinations thereof.

A specific example of one category of polyol sweeteners include sugars, in particular a sugar selected from the group consisting of dextrose, sucrose, maltose, fructose, lactose, and combinations thereof.

A method of manufacturing extruded chewing gum may be as follows:

Gum bases are typically prepared by adding an amount of the elastomer, elastomer plasticizer and filler to a heated (100° C.-120° C.) sigma blade mixer with a front to rear speed ratio of from about 1.2:1 to about 2:1, the higher ratio typically being used for gum base which requires more rigorous compounding of its elastomers.

The initial amounts of ingredients comprising the initial mass may be determined by the working capacity of the mixing kettle in order to attain a proper consistency and by the degree of compounding desired to break down the elastomer and increase chain branching. The higher the level of filler at the start or selection of a filler having a certain particle size distribution, the higher the degree of compounding and thus more of the elastomeric chain crosslinking are broken, causing more branching of the elastomer thus lower viscosity gum bases and thus softer final gum base and gum made from such a gum base. The longer the time of compounding, the use of lower molecular weight or softening point gum base ingredients, the lower the viscosity and firmness of the final gum base.

Compounding typically begins to be effective once the ingredients have massed together. Anywhere from 15 minutes to 90 minutes may be the length of compounding time.

Preferably, the time of compounding is from 20 minutes to about 60 minutes. The amount of added elastomer plasticizer depends on the level of elastomer and filler present. If too much elastomer plasticizer is added, the initial mass becomes over plasticized and not homogeneous.

After the initial ingredients have massed homogeneously and compounded for the time desired, the balance of the gum base ingredients are added in a sequential manner until a completely homogeneous molten mass is attained. Typically, any remainder of elastomer, elastomer plasticizer and filler, are added within 60 minutes after the initial compounding time. The filler and the elastomer plasticizer would typically be individually weighed and added in portions during this time. The optional waxes, softeners and antioxidants are typically added after the elastomer and elastomer plasticizers and during the next 60 minutes. Then the mass is allowed to become homogeneous before dumping.

Typical gum base processing times may vary from about one to about three hours, preferably from about 1½ to 2½ hours, depending on the formulation. The final mass temperature when dumped may be between 70° C. and 130° C. and preferably between 100° C. and 120° C. The completed molten mass is emptied from the mixing kettle into coated or lined pans, extruded or cast into any desirable shape and allowed to cool and solidify. Those skilled in the art will recognize that many variations of the above described procedure may be followed.

The water-soluble portion of the chewing gum may comprise softeners, sweeteners, high intensity sweeteners, flavoring agents, acidulants, fillers, antioxidants, and other components that provide desired attributes. Softeners typically constitute from about 0.5% to about 25.0% by weight of the chewing gum. The bulking agents generally comprise from about 5% to about 90%, preferably from about 20% to about 80% of the chewing gum. High-intensity sweeteners in gum typically may range from about 0.01 to 0.50 weight percent. A flavoring agent may be present in the chewing gum in an amount within the range of from about 0.1 to about 15.0 weight percent of the gum.

In general, chewing gum may be manufactured by sequentially adding the various chewing gum ingredients to a commercially available mixer known in the art where the finished gum base is already present. After the initial ingredients have been thoroughly mixed, the gum mass is discharged from the mixer and shaped into the desired form such as by rolling into sheets and cutting into sticks, extruded into chunks or casting into pellets.

Generally, the ingredients may be mixed by first melting the gum base and adding it to the running mixer. Colors, active agents and/or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor have been added.

The entire mixing procedure typically takes from thirty to forty minutes, but longer mixing times may sometimes be required. Those skilled in the art will recognize that many variations of the above described procedure may be followed.

In accordance with the invention, the chewing gum may comprise about 0.1 to about 75% by weight of an outer coating applied onto the chewing gum centre. Thus, suitable coating types include hard coatings, film coatings and soft coatings of any composition including those currently used in coating of chewing gum.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the consumer and it may moreover protect the gum centres for various reasons. In a typical process of providing the chewing gum centres with a protective sugar coating, the gum centres are successively treated in suitable coating equipment with aqueous solutions of crystallisable sugar such as sucrose or dextrose, which, depending on the stage of coating reached, may contain other functional ingredients, e.g. fillers, binding agents, colours, etc. In the present context, the sugar coating may contain further functional or active compounds including flavour compounds and/or active compounds.

In a typical hard coating process as it will be described in detail in the following, a suspension containing crystallisable sugar and/or polyol is applied onto the gum centres and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished chewing gum element, such as about 10 to about 60% by weight, including about 15 to about 50% by weight.

In further useful embodiments, the outer coating of the chewing gum element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to a chewing gum centre of any of the above forms. The thickness of such a coating is usually between 20 and 100 µm. Generally, the film coating is obtained by passing the chewing gum centres through a spray zone with atomized droplets of the coating materials in a suitable aqueous or organic solvent vehicle, after which the material adhering to the gum centres is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers, also referred to as functional polymers are polymers that, in addition to its film-forming characteristics, confer a modified release performance with respect to active components of the chewing gum formulation. Such release modifying polymers include methylacrylate ester copolymers, ethylcellulose (EC) and enteric polymers designed to resist the acidic stomach environment. The latter group of polymers include: cellulose acetate phthalate (CAP), polyvinyl acetate phthalate (PVAP), shellac, methacrylic acid copolymers, cellulose acetate trimellitate (CAT) and HPMC. It will be appreciated that the outer film coating according to the present invention may comprise any combination of the above film-coating polymers.

According to the invention, the one or more cannabinoids may be selected from various cannabinoids.

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that the additional components such as secondary and minor cannabinoids and the non-cannabinoid fraction have been removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the cannabis plant and purified to the extent that other cannabinoids and non-cannabinoid components that are co-extracted with the cannabinoids have been substantially removed, such that the highly purified cannabinoid is greater than or equal to 95% (w/w) pure.

"Plant material" is defined as a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

In the context of this application the terms "cannabinoid extract" or "extract of cannabinoids", which are used interchangeably, encompass "Botanical Drug Substances" derived from cannabis plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of cannabis, "botanical drug substances" derived from cannabis plants do not include highly purified, Pharmacopoeial grade cannabinoids.

The term "Cannabis plant(s)" encompasses wild type Cannabis sativa and also variants thereof, including cannabis chemovars which naturally contain different amounts of the individual cannabinoids, Cannabis sativa subspecies indica including the variants var. indica and var. kafiristanica, Cannabis indica, Cannabis ruderalis and also plants which are the result of genetic crosses, self-crosses or hybrids thereof The term "Cannabis plant material" is to be interpreted accordingly as encompassing plant material derived from one or more cannabis plants. For the avoidance of doubt it is hereby stated that "cannabis plant material" includes dried cannabis biomass.

Preferably the one or more cannabinoids are selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC. This list is not exhaustive and merely details the cannabinoids which are identified in the present application for reference.

So far, more than 120 different phytocannabinoids have been identified which are within the scope of the present invention.

Cannabinoids can be split into different groups as follows: Phytocannabinoids; Endocannabinoids; and Synthetic cannabinoids.

Cannabinoid receptors can be activated by three major groups of agonist ligands, for the purposes of the present invention and whether or not explicitly denominated as such herein, lipophilic in nature and classed respectively as: endocannabinoids (produced endogenously by mammalian cells); phytocannabinoids (such as cannabidiol, produced by the cannabis plant); and, synthetic cannabinoids (such as HU-210).

Phytocannabinoids can be found as either the neutral carboxylic acid form or the decarboxylated form depending on the method used to extract the cannabinoids. For example, it is known that heating the carboxylic acid form will cause most of the carboxylic acid form to decarboxylate.

Phytocannabinoids can also occur as either the pentyl (5 carbon atoms) or propyl (3 carbon atoms) variant. For example, the phytocannabinoid THC is known to be a CB1 receptor agonist whereas the propyl variant THCV has been discovered to be a CB1 receptor antagonist meaning that it has almost opposite effects.

According to the invention, examples of phytocannabinoids may be cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC.

The formulation according to the present invention may also comprise at least one cannabinoid selected from those disclosed in A. Douglas Kinghorn et al., Phytocannabinoids, Vol. 103, Chapter 1, pages 1-30.

Examples of endocannabinoids are molecules that activate the cannabinoid receptors within the body Examples include 2-arachidonyl glycerol (2AG), 2-arachidonyl glyceryl ether (2AGE), arachidonyl dopamine, and arachidonyl ethanolamide (anandamide). Structurally related endogenous molecules have been identified that share similar structural features, but that display weak or no activity towards the cannabinoid receptors but are also termed endocannabinoids. Examples of these endocannabinoid lipids include 2-acyl glycerols, alkyl or alkenyl glyceryl ethers, acyl dopamines and N-acylethanolamides that contain alternative fatty acid or alcohol moieties, as well as other fatty acid amides containing different head groups. These include N-acylserines as well as many other N-acylated amino acids. Examples of cannabinoid receptor agonists are neuromodulatory and affect short-term memory, appetite, stress response, anxiety, immune function and analgesia. Synthetic cannabinoids encompass a variety of distinct chemical classes: the cannabinoids structurally related to THC, the cannabinoids not related to THC, such as (cannabimimetics) including the aminoalkylindoles, 1,5-diarylpyrazoles, quinolines, and arylsulfonamides, and eicosanoids related to the endocannabinoids. All or any of these cannabinoids can be used in the present invention.

It is preferred that the formulation comprises one or two primary cannabinoids, which are preferably selected from the group consisting of, cannabidiol (CBD) or cannabidivarin (CBDV), tetrahydrocannabinol (THC), tetrahydrocannabivarin (THCV), tetrahydrocannabinolic acid (THCA), cannabigerol (CBG) and cannabidiolic acid (CBDA) or a combination thereof. It is preferred that the formulation comprises cannabidiol and/or tetrahydrocannabinol.

Preferably, the chewing gum of the present invention may be used for the treatment or alleviation of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In a further aspect of the present invention the oral cannabinoid formulation is suitable for use in the treatment of conditions requiring the administration of a neuroprotectant or anti-convulsive medication.

The oral cannabinoid formulation may be for use in the treatment of seizures.

The oral cannabinoid formulation may be for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, cannabis use disorder, post-traumatic stress disorder, anxiety, early psychosis, Alzheimer's disease, and autism.

The following non-limiting examples illustrate different variations of the present invention. The examples are meant for indicating the inventive concept; hence the mentioned examples should not be understood as exhaustive for the present. In particular, CBD is used as an exemplary compound, but may also be another cannabinoid.

EXAMPLES

Example 1

Preparation of Gum Base

Twenty different water-insoluble gum bases were prepared. The gum bases were prepared in the process as described below. In the subsequent examples, the specific compositions of the gum bases (GB10 to GB29) are outlined.

Elastomers and elastomer plasticizer (PVA) were mixed at 120° C. together with filler, either calcium carbonate or talc, in a mixer having horizontally placed Z-shaped arms for mixing. It is noted that PVA was applied as an elastomer plasticizer for the elastomers in the composition and not in form of an elastomer. PVA as an elastomer plasticizer has special properties in the present context. For some of the comparative examples, another comparative polymer was added together with the elastomers and elastomer plasticizer and mixed together with the elastomer and the elastomer plasticizer.

Natural resins were added after about 30 minutes of mixing of the polymers. After the polymers and the natural resin had softened in the composition, additional ingredients were added, such as triacetin, emulsifier, wax, antioxidants and vegetable fat.

After a total mixing time of about 45-60 minutes, the mixture was discharged into a pan and allowed to cool at room temperature.

For some of the examples where butyl rubber (BR) was added as an elastomer, the mixing time was optionally extended to a total of about 90-105 minutes depending on the amount of optional fillers.

In all of the gum base examples, the amount of the various ingredients is given as % by weight of the gum base.

Example 2

Various Gum Base Formulations

TABLE 1A

| GB number | GB10 | GB11 | GB12 | GB13 | GB14 |
|---|---|---|---|---|---|
| PVA | 25 | 18 | 30 | 10 | 40 |
| PIB | 5 | 10 | 5 | 10 | 5 |
| BR | 5 | 5 | 5 | 5 | — |
| Nat. resin | 25 | 20 | 20 | 35 | 15 |
| Calcium Carbonate | 17 | — | 17 | 17 | 17 |
| Talc | — | 17 | — | — | — |
| Triacetin | — | 7 | — | — | — |
| Emulsifier | 5 | 10 | 5 | 5 | 5 |
| Wax | 13 | 13 | 13 | 13 | 13 |
| Veg. fat | 5 | — | 5 | 5 | 5 |
| Total | 100 | 100 | 100 | 100 | 100 |

Gum base compositions, PVA = polyvinyl acetate (Vinnapas B 1.5 sp., supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat.

Example 3

Various Gum Base Formulations

TABLE 1B

| GB number | GB15 | GB16 | GB17 | GB18 | GB19 |
|---|---|---|---|---|---|
| PVA | 25 | 25 | 20 | 40 | 15 |
| PIB | 5 | 10 | 5 | 5 | 5 |
| BR | 5 | 5 | 5 | 5 | — |
| Nat. resin | 25 | 20 | 30 | 10 | 40 |
| Calcium Carbonate | 17 | 17 | 17 | 17 | 17 |
| Talc | — | — | — | — | — |
| Triacetin | — | — | — | — | — |
| Emulsifier | 5 | 5 | 5 | 5 | 5 |
| Wax | 13 | 13 | 13 | 13 | 13 |
| Veg. fat | 5 | 5 | 5 | 5 | 5 |
| Total | 100 | 100 | 100 | 100 | 100 |

Gum base compositions, PVA = polyvinyl acetate (Vinnapas B 1.5 sp., supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat.

Example 4

Various Gum Base Formulations

TABLE 1C

| GB number | GB20 | GB21 | GB22 | GB23 | GB24 |
|---|---|---|---|---|---|
| PVA | 18 | 18 | 18 | 18 | 18 |
| PIB | 10 | 10 | 10 | 10 | 10 |
| BR | 5 | 5 | 5 | 5 | 5 |
| Nat. resin | 20 | 20 | 20 | 20 | 20 |
| Calcium Carbonate | — | — | — | — | — |
| Talc | 14 | 16.5 | 13.5 | 17 | 14 |

TABLE 1C-continued

| GB number | GB20 | GB21 | GB22 | GB23 | GB24 |
|---|---|---|---|---|---|
| Triacetin | 7 | 7 | 7 | 7 | 7 |
| Emulsifier | 10 | 10 | 10 | 10 | 10 |
| Wax | 13 | 13 | 13 | 13 | 13 |
| Veg. fat | — | — | — | — | — |
| Acesulfame | — | 0.5 | 0.5 | — | — |
| Menthol | 3 | — | 3 | — | 3 |
| BHT | — | — | — | 0.04 | 0.04 |
| Total | 100 | 100 | 100 | 100 | 100 |

Gum base compositions, PVA = polyvinyl acetate (Vinnapas B 1.5 sp., supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat; Acesulfame K (HIS = high-intensity sweetener); Menthol (flavor); BHT (Butylated hydroxytoluene = antioxidant).

Example 5

Various Gum Base Formulations

TABLE 1D

| GB number | GB25 | GB26 | GB27 | GB28 | GB29 |
|---|---|---|---|---|---|
| PVA | 25 | 18 | 30 | 30 | 20 |
| PIB | 5 | 10 | 5 | 3 | 3 |
| BR | 5 | 5 | — | 2 | 2 |
| Nat. resin | 25 | 20 | — | — | 20 |
| VA-VL | — | — | 20 | 20 | 10 |
| Calcium Carbonate | 17 | — | 17 | 17 | 17 |
| Talc | — | 17 | — | — | — |
| Triacetin | — | 7 | — | — | 2 |
| Emulsifier | 5 | 10 | 11 | 11 | 9 |
| Wax | 13 | 13 | 12 | 12 | 12 |
| Veg. fat | 5 | — | 5 | 5 | 5 |
| Total | 100 | 100 | 100 | 100 | 100 |

Gum base compositions, PVA = polyvinyl acetate (Vinnapas B 1.5 sp., supplied by Wacker); PIB = polyisobutylene (Oppanol B12, supplied by BASF); BR = butyl rubber (isobutylene-isoprene copolymer); Nat. resin = glycerol ester of hydrogenated gum rosin; VA-VL = vinyl acetate-vinyl laurate copolymer (Vinnapas B 500/40 VL, supplied by Wacker); Veg. fat = vegetable fat.

Example 6

CBD Extract 52%

CBD extract with a 52% content of CBD provided by CBDepot (batch number CSFF 2018/5) was preheated to around 60° C. for around 0.5 to 1 hour until the extract was in liquid form. The extract had a content of fatty acids, glycerol, waxes, terpenes and flavonoids. After the preheating process, the extract was either used directly together with additional chewing gum ingredients, or the extract was applied in a premix.

Example 7

CBD Extract 10%

CBD extract with a 10% content of CBD provided by Medical Hemp (batch number MH131B Gold), was preheated to around 60° C. for around 0.5 to 1 hour until the extract was in liquid form. The extract had a content of fatty acids, glycerol, waxes, terpenes and flavonoids. After the preheating process, the extract was either used directly together with additional chewing gum ingredients, or the extract was applied in a premix.

Example 8

CBD Isolate

CBD isolate from cannabis plant tissues (phytocannabinoid) with a 98.5% content of CBD provided by Medical Hemp (batch number MH18212) was dissolved in an 96% ethanol solution. The ratio between the CBD isolate and ethanol was 1:1. Once CBD was dissolved in the ethanol, the CBD isolate was either used directly together with additional chewing gum ingredients, or the extract was applied in a premix.

Example 9

Preparation of Cannabinoid Sugar Alcohol Premix

A premix was made with CBD and sugar alcohol particles, here sorbitol. The premix was made in a weight ratio of 1:5 of CBD and sorbitol with either one of the forms of CBD outlined in Examples 6-8. CBD was added to the sugar alcohol particles and homogenized gently.

Example 10

Preparation of Cannabinoid Cyclodextrin Premix

CBD (extract or isolate) was added and dissolved in a 5% solution of polysorbate 80 to obtain a 10% solution of CBD. The 10% CBD solution is slowly added and mixed into a solution with 10% cyclodextrin to form a CBD-cyclodextrin complex. The water is removed, whereupon the complex was either used directly together with additional chewing gum ingredients, or the complex was applied in a premix.

Example 11

Preparation of Cannabinoid Microcrystalline Cellulose Premix

A cannabinoid-microcrystalline cellulose (MCC) premix was made by first adding free cannabinoid to poloxamer F68 (PF) to obtain a 10% blend of cannabinoid in poloxamer F68. Butylated hydroxytoluene (BHT) was added (0.5%) to 50 grams of the cannabinoid-poloxamer F68 solid mix and added to 50 grams of microcrystalline cellulose provided as Avicel PH 102 from FMC Biopolymer. This was then mixed in a Kitchenaid mixer operated at about 30 RPM for about 30 minutes at room temperature. This mixture was equilibrated for about 30 minutes in a sealed container. Hereby, at 5% cannabinoid-MCC premix was obtained.

Example 12

Preparation of Cannabinoid Chewing Gum Formulation

Gum base (GB) prepared according to Example 1 and formulated according to Examples 2-5 was mixed with filler, here either talc, calcium carbonate or sugar alcohol, in a 60 g mixer having horizontally placed Z-shaped arms for mixing. The mixer was preheated to a temperature of approximately 50° C. Once the content of the mixer was homogeneous, chewing gum ingredients were added according to a specified time schedule.

Example 13

Preparation of Cannabinoid Chewing Gum Formulation with Specific Order

Gum base (GB) prepared according to Example 1 and formulated according to Examples 2-5 was mixed with a filler, here sugar alcohol, in a 60 g mixer having horizontally placed Z-shaped arms for mixing. The mixer was preheated to a temperature of approximately 50° C. Once the content of the mixer was homogeneous, chewing gum ingredients, including water-soluble ingredient, and cannabinoids were added according to a specified time schedule as follows:

TABLE 1E

It was secured that CBD was thoroughly mixed into the composition and that a homogeneous mixture was obtained. Sugar alcohol* was prepared as a premix with CBD according to Example 9. Here, the content in weight % is calculated as the sugar alcohol content, excluding the CBD content in the premix. CBD 52%* was prepared according to Example 6.
Specified order of addition in the preparation of chewing gum

| Ingredient | Content in weight % | Application time in min. |
|---|---|---|
| Gum base (GB) | 40 | 0 |
| Sugar alcohol | 22.8 | 0 |
| Maltitol syrup | 8 | 3 |
| Menthol powder | 3 | 5 |
| Eucalyptus Powder | 2 | 5 |
| Acesulfame k | 0.1 | 5 |
| Sucralose | 0.1 | 5 |
| Sugar alcohol* | 5 | 8 |
| CBD 52%* | 1 | 8 |
| Sugar alcohol | 18 | 8 |
| Total | 100 | 13 |

Example 14

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1F

It was secured that CBD was thoroughly mixed into the composition and that a homogeneous mixture was obtained. CBD 52%* was prepared according to Example 6.

| CG Number | CG100 | CG101 | CG102 | CG103 | CG104 |
|---|---|---|---|---|---|
| GB10 | 40 | — | — | — | — |
| GB11 | — | 40 | — | — | — |
| GB12 | — | — | 40 | — | — |
| GB13 | — | — | — | 40 | — |
| GB14 | — | — | — | — | 40 |
| Sorbitol | 45.8 | 45.8 | 45.8 | 45.8 | 45.8 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD 52%* | 1 | 1 | 1 | 1 | 1 |
| Total | 100 | 100 | 100 | 100 | 100 |

Example 15

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1G

It was secured that CBD was thoroughly mixed into the composition and that a homogeneous mixture was obtained. CBD 52%* was prepared according to Example 6.

| CG Number | CG105 | CG106 | CG107 | CG108 | CG109 |
|---|---|---|---|---|---|
| GB15 | 40 | — | — | — | — |
| GB16 | — | 40 | — | — | — |
| GB17 | — | — | 40 | — | — |
| GB18 | — | — | — | 40 | — |
| GB19 | — | — | — | — | 40 |
| Sorbitol | 45.8 | 45.8 | 45.8 | 45.8 | 45.8 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD 52%* | 1 | 1 | 1 | 1 | 1 |
| Total | 100 | 100 | 100 | 100 | 100 |

Example 16

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1H

It was secured that CBD was thoroughly mixed into the composition and that a homogeneous mixture was obtained. CBD 52%* was prepared according to Example 6.

| CG Number | CG110 | CG111 | CG112 | CG113 | CG114 |
|---|---|---|---|---|---|
| GB20 | 40 | — | — | — | — |
| GB21 | — | 40 | — | — | — |
| GB22 | — | — | 40 | — | — |
| GB23 | — | — | — | 40 | — |
| GB24 | — | — | — | — | 40 |
| Sorbitol | 45.8 | 45.8 | 45.8 | 45.8 | 45.8 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD 52%* | 1 | 1 | 1 | 1 | 1 |
| Total | 100 | 100 | 100 | 100 | 100 |

Example 17

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1I

It was secured that CBD was thoroughly mixed into the composition and that a homogeneous mixture was obtained. CBD 52%* was prepared according to Example 6.

| CG Number | CG115 | CG116 | CG117 | CG118 | CG119 |
|---|---|---|---|---|---|
| GB25 | 40 | — | — | — | — |
| GB26 | — | 40 | — | — | — |
| GB27 | — | — | 40 | — | — |
| GB28 | — | — | — | 40 | — |
| GB29 | — | — | — | — | 40 |
| Sorbitol | 45.8 | 45.8 | 45.8 | 45.8 | 45.8 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD 52%* | 1 | 1 | 1 | 1 | 1 |
| Total | 100 | 100 | 100 | 100 | 100 |

Example 18

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1J

It was secured that CBD was thoroughly mixed into the composition and that a homogeneous mixture was obtained. CBD 52%* was prepared according to Example 6.

| CG Number | CG120 | CG121 | CG122 | CG123 | CG124 |
|---|---|---|---|---|---|
| GB10 | 40 | 40 | — | — | — |
| GB11 | — | — | 40 | 40 | 40 |
| Sorbitol | 30 | 45.8 | 30 | 35.8 | 45.8 |
| Talc | 15.8 | — | 15.8 | 10 | — |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD 52%* | 1 | 1 | 1 | 1 | 1 |
| Total | 100 | 100 | 100 | 100 | 100 |

Example 19

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1K

It was secured that CBD was thoroughly mixed into the composition and that a homogeneous mixture was obtained. CBD 52%* was prepared according to Example 6.

| CG Number | CG125 | CG126 | CG127 | CG128 | CG129 |
|---|---|---|---|---|---|
| GB11 | 55.8 | 45.8 | 35.8 | 25.8 | 15.8 |
| Sorbitol | 30 | 40 | 50 | 60 | 70 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD 52%* | 1 | 1 | 1 | 1 | 1 |
| Total | 100 | 100 | 100 | 100 | 100 |

Example 20

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1L

It was secured that CBD was thoroughly mixed into the composition and that a homogeneous mixture was obtained. CBD isolate* was prepared according to Example 8. CBD 10%* was prepared according to Example 7. CBD 52%* was prepared according to Example 6.

| CG Number | CG130 | CG131 | CG132 | CG133 | CG134 |
|---|---|---|---|---|---|
| GB10 | 40 | 40 | — | — | — |
| GB11 | — | — | 40 | 40 | 40 |
| Sorbitol | 41.8 | 45.8 | 46.3 | 41.8 | 45.8 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD isolate* | — | — | 0.5 | — | — |
| CBD 10%* | 5 | — | — | 5 | — |
| CBD 52%* | — | 1 | — | — | 1 |
| Total | 100 | 100 | 100 | 100 | 100 |

Example 21

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1M

It was secured that CBD was thoroughly mixed into the composition and that a homogeneous mixture was obtained. CBD 52%* was prepared according to Example 6.

| CG Number | CG135 | CG136 | CG137 | CG138 | CG139 |
|---|---|---|---|---|---|
| GB11 | 40 | 40 | 40 | 40 | 40 |
| Sorbitol | 45.8 | 45.6 | 45.4 | 45.2 | 45.0 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.2 | 0.3 | 0.4 | 0.5 |
| Sucralose | 0.1 | 0.2 | 0.3 | 0.4 | 0.5 |
| CBD 52%* | 1 | 1 | 1 | 1 | 1 |
| Total | 100 | 100 | 100 | 100 | 100 |

Example 22

Composition of Cannabinoid Chewing Gum

Cannabinoid chewing gum based on the procedure in Example 13 was made with the formulations outlined in the examples below. The formulations were formed into chewing gum pieces by extrusion (rolling and scoring). The extruded chewing gum pieces had a weight of 1 g for each piece and a content of CBD of 5 mg for each piece. In all of the chewing gum examples, the amount of the various ingredients is given as % by weight of the chewing gum.

TABLE 1N

It was secured that CBD was thoroughly mixed into the composition and that a homogeneous mixture was obtained. CBD 52%* was prepared according to Example 6. CBD-MCC 5%* was prepared according to Example 11. CBD-MCC 10%* was prepared according to Example 11 with a higher amount of CBD. CBD-cyclodex* is CBD-cyclodextrin complex prepared according to Example 10. Self-emulsifying* was prepared with an emulsifier, here polysorbate.

| CG Number | CG140 | CG141 | CG142 | CG143 | CG144 |
|---|---|---|---|---|---|
| GB11 | 40 | 40 | 40 | 40 | 40 |
| Sorbitol | 45.8 | 36.8 | 41.8 | 26.8 | 44.8 |
| Maltitol syrup | 8 | 8 | 8 | 8 | 8 |
| Menthol powder | 3 | 3 | 3 | 3 | 3 |
| Eucalyptus Powder | 2 | 2 | 2 | 2 | 2 |
| Acesulfame k | 0.1 | 0.1 | 0.1 | 0.1 | 0.1 |
| Sucralose | 0.1 | 0.1 | 0.1 | 0.1 | 0.1 |
| CBD 52%* | 1 | — | — | — | 1 |
| CBD-MCC 5%* | — | 10 | — | — | — |
| CBD-MCC 10%* | — | — | 5 | — | — |
| CBD-cyclodex* | — | — | — | 20 | — |
| Self-emulsifying* | — | — | — | — | 1 |
| Total | 100 | 100 | 100 | 100 | 100 |

Example 23

Coating of Chewing Gum

A hard coating was prepared for selected samples with the following composition:

TABLE 1O

It was secured that CBD was thoroughly mixed into the composition and that a homogeneous mixture was obtained. CBD 52%* was prepared according to Example 6. CBD isolate* was prepared according to Example 8. The coating was provided to samples of CG100 from Example 15.

Hard coating

| | % by weight Number | |
|---|---|---|
| Ingredients | CG145 | CG146 |
| Maltitol | 57 | 57 |
| Water | 25.4 | 25.9 |
| Mannitol | 11 | 11 |
| gummi arabicum | 4 | 4 |
| titandioxid | 1 | 1 |
| Polysorbate | 0.1 | 0.1 |
| CBD 52%* | 1.5 | — |
| CBD isolate* | — | 0.7 |
| Total | 100 | 100 |

The coating was applied as a pre-heated suspension as outlined above to 1 g extruded chewing gum with the formulation of CG100 in Example 15, except that CBD 52% or CBD isolate was substituted with sorbitol in CG100. Hence, CBD was not present in the extruded gum, but only in the coating. A total of 5 mg CBD was present in the coated tablet. The suspension was applied in 3 subsequent steps according to conventional coating techniques to a total of 0.45 g coating to the 1 g extruded gum. This corresponds to a ratio of extruded gum to coating on 70:30.

Example 24

In Vivo Testing of Release

A sample was chewed with a chewing frequency of 60 chews pr. minute for 3 or 5 minutes in a test panel of 8 test persons. The test person was a healthy person appointed on an objective basis according to specified requirements. After 3 or 5 minutes, the content of CBD was measured in the remaining chewing gum residue. The chewing gum was subject to triple measurements for each of the 8 test persons, giving a total of 24 measurements for each sample. An average of the 24 measurements was calculated and the weight % release was calculated based on the original content of CBD in the sample. The content of CBD was measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly to an HPLC system and analyzed by an assay method.

Example 25

In Vitro Testing of Release

In vitro release of CBD was established by means of a chewing machine (Dissolution Test for Chewing Gums, General Monograph 2.9.25. In European Pharmacopoeia, 5th ed). A chewing chamber was filled with 20 ml buffer (phosphate buffer pH 7.4). The chewing gum sample was placed in the chamber and the chewing machine was initiated at 20 degree Celsius with 1 chew per second. After 3 or 5 minutes of chewing, the machine was stopped and the chewing gum sample (residue) was placed in a vial. If more release time points are needed (release profile), the chewing buffer must be exchanged with 20 ml of fresh buffer every five minutes. The content of CBD was measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method.

Example 26

Stability Testing Method

For stability testing, the ICH guideline is used; 25° C./60% RH (2 years), 30° C./65% RH (1 year), 40° C./75% RH (3 month). All samples were packed in duma bottles before stored in the conditions. All samples were sensorially and analytically evaluated. The content of CBD was measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC set-up and analyzed by an assay method. The following method was able to separate and quantify CBD, delta-9 THC, delta-8 THC and CBN.

Example 27

CBD Delivered to the Oral Mucosa

A sample was chewed in vivo with a chewing frequency of 60 chews pr. minute for 5 minutes in a test panel of 8 test persons. The test person was not allowed to swallow during the procedure. After one minute, saliva was obtained from the test person and collected in a vessel for later analysis. In tests for 5 minutes release, the same procedure was followed until 5 minutes where the last sample was collected and added to the same vessel for aggregated analysis. The test person was a healthy person appointed on an objective basis according to specified requirements. the aggregated saliva sample was collected after 5 minutes, the content of CBD was measured in the saliva. The content of CBD was also measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method. The gum and saliva was subject to 3 triple measurements for each of the 8 test persons, giving a total of 24 measurement for each sample. An average of the 24 measurements was calculated and the weight % release was calculated. By comparing the amount of CBD in the remaining chewing gum residue and the amount of CBD in the saliva, the amount of CBD delivered to the oral mucosa could be estimated.

Example 28

Sensory Evaluation Test Set-Up

Apart from release measurements, either in vivo or in vitro, as well as stability tests of the extruded chewing gum, sensory tests were also performed to reveal very important characteristics and properties of the extruded chewing gum. These sensory parameters are important as indicators of the structure of the chewing gum composition and the behavior of the gum when chewed. The structure is the underlying guidance as to how the chewing gum resembles the structure of a comparative chewing gum, which is set as the standard in the test series, i.e. the chewing gums are compared to each other in the test series. The test set-up was composed of 8 test persons in a test panel. Each of the test persons were healthy individuals appointed on an objective basis according to specified requirements. The sensory analysis was performed according to ISO 4121-2003 in testing conditions following ISO 8589. The result is an average of the results of the 8 individuals.

The test persons gave a rating from "+" to "+++++", where "+" is poor and "+++++" is excellent and comparable to the standard, i.e. "+++++" means that the gum was comparable to the standard and "+" means that the gum was very far from comparable to the standard. "0" indicated that it was not tested.

Five different parameters were tested in a test panel:

| Initial chew | Texture | Flavor | Sweetness | Off-notes |
| --- | --- | --- | --- | --- |

"Initial chew"—the first impression of the gum when chewed within the first 30 seconds. For instance, a very hard and viscous structure gave a very low rating and a very brittle structure also gave a very low rating.

"Texture"—the overall impression of the gum after 30 seconds of chewing gum or when the gum has gained the structure of a steady state. For instance, a very hard structure gave a very low rating and a very smooth structure also gave a very low rating.

"Flavor"—the overall impression of the gum during chewing with respect to flavor. For instance, a very low flavor experience gave a very low rating and a too high flavor experience that was not comparable to the standard also gave a very low rating.

"Sweetness"—the overall impression of the taste of the gum during chewing with respect to sweetness. For instance, if the sweetness was decreasing rapidly a very low rating was given and if the sweetness was too high giving an uncomfortable feeling a very low rating was also given.

"Off-notes"—the overall impression of the off-note from the one or more cannabinoids in the composition during chewing. For instance, if off-notes (grass, bitter notes, irritation in the throat) were experienced in the throat, a low rating was given and if other uncomfortable sensations was experienced a low rating was also given.

Example 29

Sensory Evaluation of Cannabinoid Chewing Gum

TABLE 2A

Evaluation of Examples 14-22 according to Example 28.

| CG | Initial chew | Texture | Flavor | Sweetness | Off-notes |
| --- | --- | --- | --- | --- | --- |
| CG 100 | +++++ | +++++ | ++++ | ++++ | ++++ |
| CG 101 | +++++ | +++++ | ++++ | ++++ | ++++ |
| CG 102 | +++++ | +++++ | ++++ | ++++ | ++++ |

TABLE 2A-continued

Evaluation of Examples 14-22 according to Example 28.

| CG | Initial chew | Texture | Flavor | Sweetness | Off-notes |
|---|---|---|---|---|---|
| CG 103 | ++++ | +++ | +++ | ++++ | ++++ |
| CG 104 | ++++ | ++++ | ++++ | +++ | ++++ |
| CG 105 | +++++ | +++++ | ++++ | ++++ | ++++ |
| CG 106 | +++++ | +++++ | ++++ | ++++ | ++++ |
| CG 107 | +++++ | +++++ | ++++ | ++++ | ++++ |
| CG 108 | ++++ | +++ | +++ | +++ | +++ |
| CG 109 | +++ | ++++ | ++++ | +++ | +++ |
| CG 110 | 0 | 0 | +++++ | ++++ | +++++ |
| CG 111 | 0 | 0 | ++++ | +++++ | +++++ |
| CG 112 | 0 | 0 | +++++ | +++++ | +++++ |
| CG 113 | 0 | 0 | ++++ | ++++ | ++++ |
| CG 114 | 0 | 0 | +++++ | ++++ | +++++ |
| CG 115 | +++++ | +++++ | ++++ | ++++ | ++++ |
| CG 116 | +++++ | +++++ | ++++ | ++++ | ++++ |
| CG 117 | ++ | + | ++ | + | + |
| CG 118 | + | + | ++ | + | + |
| CG 119 | ++ | ++ | +++ | +++ | ++ |
| CG 120 | ++++ | ++++ | ++ | ++ | ++ |
| CG 121 | +++++ | +++++ | ++++ | ++++ | ++++ |
| CG 122 | ++++ | ++++ | ++ | ++ | ++ |
| CG 123 | +++++ | ++++ | ++++ | ++++ | ++++ |
| CG 124 | +++++ | +++++ | ++++ | ++++ | ++++ |
| CG 125 | ++++ | ++++ | ++++ | ++++ | ++++ |
| CG 126 | ++++ | ++++ | ++++ | ++++ | +++ |
| CG 127 | +++++ | ++++ | ++++ | ++++ | ++++ |
| CG 128 | ++++ | ++++ | ++++ | ++++ | ++++ |
| CG 129 | +++ | +++ | +++ | +++ | +++ |
| CG 130 | ++++ | ++++ | ++++ | ++++ | ++++ |
| CG 131 | +++++ | +++++ | ++++ | ++++ | ++++ |
| CG 132 | +++++ | +++++ | +++++ | +++ | +++ |
| CG 133 | +++++ | +++++ | +++++ | +++++ | +++++ |
| CG 134 | +++++ | +++++ | ++++ | ++++ | ++++ |
| CG 135 | +++++ | +++++ | ++++ | ++++ | ++++ |
| CG 136 | +++++ | +++++ | ++++ | ++++ | ++++ |
| CG 137 | +++++ | +++++ | +++ | +++ | +++ |
| CG 138 | +++++ | +++++ | +++ | ++ | +++ |
| CG 139 | +++++ | +++++ | ++ | + | +++ |
| CG 140 | +++++ | +++++ | ++++ | ++++ | ++++ |
| CG 141 | +++++ | +++++ | ++++ | ++++ | ++++ |
| CG 142 | ++++ | ++++ | ++++ | ++++ | ++++ |
| CG 143 | +++++ | +++++ | +++++ | +++++ | +++++ |
| CG 144 | +++++ | +++++ | +++++ | +++++ | +++++ |

Example 30

Release of Cannabinoid from Extruded Chewing Gum

TABLE 2B

Chewing gum samples from Example 14 was tested for release after 3 or 5 minutes of in vivo chewing according to the test method of Example 24. The value indicates weight % of cannabinoid released from the chewing gum sample (CG).

| CG Number | CG100 | CG101 | CG102 | CG103 | CG104 |
|---|---|---|---|---|---|
| 3 minutes | 12 | 11 | 12 | 8 | 7 |
| 5 minutes | 17 | 16 | 17 | 12 | 11 |

TABLE 2C

Chewing gum samples from Example 15 was tested for release after 3 or 5 minutes of in vitro chewing according to the test method of Example 25. The value indicates weight % of cannabinoid released from the chewing gum sample (CG).

| CG Number | CG100 | CG101 | CG102 | CG103 | CG104 |
|---|---|---|---|---|---|
| 3 minutes | 13 | 12 | 14 | 7 | 6 |
| 5 minutes | 15 | 14 | 16 | 11 | 10 |

The result shows that in the outer end of the ranges according to the invention, the release was lower, but still acceptable (CG103 and CG104). However, the ranges should be seen combined, such that the range of each of elastomer plasticizers and natural resin contributes in combination to the overall effect and release properties of the chewing gum. Hence, if an amount in the end of the range for natural resin is applied, the amount of elastomer plasticizer may to some extend counteract the negative effect.

Example 31

Release of Cannabinoid from Extruded Chewing Gum

TABLE 2D

Chewing gum samples from Example 15 was tested for release after 3 or 5 minutes of in vivo chewing according to the test method of Example 24. The value indicates weight % of cannabinoid released from the chewing gum sample (CG).

| CG Number | CG105 | CG106 | CG107 | CG108 | CG109 |
|---|---|---|---|---|---|
| 3 minutes | 12 | 11 | 11 | 8 | 7 |
| 5 minutes | 17 | 15 | 17 | 13 | 12 |

TABLE 2E

Chewing gum samples from Example 16 was tested for release after 3 or 5 minutes of in vitro chewing according to the test method of Example 25. The value indicates weight % of cannabinoid released from the chewing gum sample (CG).

| CG Number | CG105 | CG106 | CG107 | CG108 | CG109 |
|---|---|---|---|---|---|
| 3 minutes | 13 | 11 | 14 | 7 | 6 |
| 5 minutes | 15 | 13 | 16 | 12 | 11 |

The result shows that in the outer end of the ranges according to the invention, the release was lower, but still acceptable (CG108 and CG109). However, the ranges should be seen combined, such that the range of each of elastomer plasticizers and natural resin contributes in combination to the overall effect and release properties of the chewing gum. Hence, if an amount in the end of the range for natural resin is applied, the amount of elastomer plasticizer may to some extend counteract the negative effect.

The release of CG 110-114 was comparable to CG105-109.

Example 32

Release of Cannabinoid from Extruded Chewing Gum

TABLE 2F

Chewing gum samples from Example 17 was tested for release after 3 or 5 minutes of in vivo chewing according to the test method of Example 24. The value indicates weight % of cannabinoid released from the chewing gum sample (CG).

| CG Number | CG115 | CG116 | CG117 | CG118 | CG119 |
|---|---|---|---|---|---|
| 3 minutes | 12 | 11 | 6 | 4 | 7 |
| 5 minutes | 17 | 16 | 7 | 6 | 9 |

TABLE 2G

Chewing gum samples from Example 17 was tested for release after 3 or 5 minutes of in vitro chewing according to the test method of Example 25. The value indicates weight % of cannabinoid released from the chewing gum sample (CG).

| CG Number | CG115 | CG116 | CG117 | CG118 | CG119 |
|---|---|---|---|---|---|
| 3 minutes | 13 | 12 | 3 | 2 | 6 |
| 5 minutes | 15 | 14 | 6 | 5 | 8 |

The result is clear in the sense that addition of VA-VL to the composition provides a much lower release (CG 117-119) than by the use of the polymers and natural resin according to the present invention. In addition, the sensory properties by the use of VA-VL (see above) also makes it clear that VA-VL is not preferred.

Example 33

Release of Cannabinoid from Extruded Chewing Gum

TABLE 2H

Chewing gum samples from Example 18 was tested for release after 3 or 5 minutes of in vivo chewing according to the test method of Example 24. The value indicates weight % of cannabinoid released from the chewing gum sample (CG).

| CG Number | CG120 | CG121 | CG122 | CG123 | CG124 |
|---|---|---|---|---|---|
| 3 minutes | 7 | 12 | 6 | 10 | 11 |
| 5 minutes | 8 | 17 | 8 | 12 | 16 |

TABLE 2I

Chewing gum samples from Example 18 was tested for release after 3 or 5 minutes of in vitro chewing according to the test method of Example 25. The value indicates weight % of cannabinoid released from the chewing gum sample (CG).

| CG Number | CG120 | CG121 | CG122 | CG123 | CG124 |
|---|---|---|---|---|---|
| 3 minutes | 6 | 13 | 7 | 10 | 12 |
| 5 minutes | 7 | 15 | 8 | 11 | 14 |

The addition of talc to the composition was expected to give a higher release of CBD since it was expected that talc would provide a more porous structure to the extruded chewing gum and thereby promote better release of CBD. However, this was not seen (CG120 and CG122) and it appears that the amount of sugar alcohols is more important for release characteristics than previously expected.

Example 34

Release of Cannabinoid from Extruded Chewing Gum

TABLE 2J

Chewing gum samples from Example 19 was tested for release after 3 or 5 minutes of in vivo chewing according to the test method of Example 24. The value indicates weight % of cannabinoid released from the chewing gum sample (CG).

| CG Number | CG125 | CG126 | CG127 | CG128 | CG129 |
|---|---|---|---|---|---|
| 3 minutes | 7 | 11 | 12 | 14 | 18 |
| 5 minutes | 8 | 13 | 17 | 19 | 22 |

TABLE 2K

Chewing gum samples from Example 19 was tested for release after 3 or 5 minutes of in vitro chewing according to the test method of Example 25. The value indicates weight % of cannabinoid released from the chewing gum sample (CG).

| CG Number | CG125 | CG126 | CG127 | CG128 | CG129 |
|---|---|---|---|---|---|
| 3 minutes | 6 | 10 | 13 | 15 | 17 |
| 5 minutes | 7 | 12 | 14 | 16 | 21 |

The results shows that a too low amount of sugar alcohol in the gum (CG125) caused problems with the release of cannabinoids and that a higher amount was desirable. Overall, this was a surprise. However, a too high amount of sugar alcohol (CG129) affected other properties of the chewing gum as seen in the sensory results which was not expected.

Example 35

Release of Cannabinoid from Extruded Chewing Gum

TABLE 2L

Chewing gum samples from Example 20 was tested for release after 3 or 5 minutes of in vivo chewing according to the test method of Example 24. The value indicates weight % of cannabinoid released from the chewing gum sample (CG).

| CG Number | CG130 | CG131 | CG132 | CG133 | CG134 |
|---|---|---|---|---|---|
| 3 minutes | 19 | 12 | 8 | 18 | 11 |
| 5 minutes | 23 | 17 | 11 | 22 | 16 |

TABLE 2M

Chewing gum samples from Example 20 was tested for release after 3 or 5 minutes of in vitro chewing according to the test method of Example 25. The value indicates weight % of cannabinoid released from the chewing gum sample (CG).

| CG Number | CG130 | CG131 | CG132 | CG133 | CG134 |
|---|---|---|---|---|---|
| 3 minutes | 18 | 13 | 7 | 17 | 12 |
| 5 minutes | 22 | 15 | 10 | 21 | 14 |

The result shows that CBD 10% (CG130 and CG133) contributes with a higher release from the extruded chewing gum than CBD 52% (CG130 and CG134). This result is very surprising and appears to be a general trend that has not previously been recognized. Addition of an isolate (CG 132) resulted in a little lower release from the gum, but still acceptable. It appears unknown why the release differs as seen. This result may be used to specifically design a controlled release profile of cannabinoids. A certain amount of for instance CBD 52% together with a certain amount of CBD 10% makes it possible to design the release of CBD, given that the release profiles are different.

Example 36

Release of Cannabinoid from Extruded Chewing Gum

TABLE 2N

Chewing gum samples from Example 21 was tested for release after 3 or 5 minutes of in vivo chewing according to the test method of Example 24. The value indicates weight % of cannabinoid released from the chewing gum sample (CG).

| CG Number | CG135 | CG136 | CG137 | CG138 | CG139 |
|---|---|---|---|---|---|
| 3 minutes | 11 | 12 | 11 | 12 | 14 |
| 5 minutes | 16 | 17 | 18 | 19 | 20 |

Generally, a slightly higher release of CBD was obtained with a higher amount of high-intensity sweetener in the extruded chewing gum formulation. This was highly unexpected since the amount of high-intensity sweetener is relatively low in the extruded chewing gum. However, as seen in the sensory test above, when the amount of high-intensity sweetener is in the high end (such as CG139), it may impact other properties of the extruded chewing gum.

Example 37

Release of Cannabinoid from Extruded Chewing Gum

TABLE 2L

Chewing gum samples from Example 22 was tested for release after 3 or 5 minutes of in vivo chewing according to the test method of Example 24. The value indicates weight % of cannabinoid released from the chewing gum sample (CG).

| CG Number | CG140 | CG141 | CG142 | CG143 | CG144 |
|---|---|---|---|---|---|
| 3 minutes | 11 | 5 | 8 | 15 | 18 |
| 5 minutes | 16 | 7 | 10 | 18 | 22 |

TABLE 2M

Chewing gum samples from Example 22 was tested for release after 3 or 5 minutes of in vitro chewing according to the test method of Example 25. The value indicates weight % of cannabinoid released from the chewing gum sample (CG).

| CG Number | CG140 | CG141 | CG142 | CG143 | CG144 |
|---|---|---|---|---|---|
| 3 minutes | 12 | 6 | 9 | 14 | 20 |
| 5 minutes | 14 | 7 | 10 | 17 | 25 |

The overall result shows that release promoting systems, such as a cyclodextrin complex with CBD (CG143) or self-emulsifiers systems (CG144), may be a particular advantage according to the invention if a higher release is desirable. However, the use of microcrystalline cellulose as a carrier in a 10% MCC-system (CG142) did provide a lower overall release which was even lower for a 5% MCC-system (CG141).

Example 38

Stability test

TABLE 2N

Chewing gum sample CG132 was tested under extreme conditions, 60° C./4% RH in accordance with Example 26. In this example, CBD was present as CBD isolate in accordance with Example 8. Sorbitol was substituted with isomalt in CG132.

| | CBD | | THC | |
|---|---|---|---|---|
| CG132 | LC (mg/piece) | % LC | LC (mg/piece) | %LC |
| 0 months | 5 | 96 | 0 | 0 |
| 14 days | 5 | 94 | 0 | 0 |
| 1 month | 5 | 84 | 0 | 0 |
| 3 months | 5 | 56 | 0 | 0 |

In comparative studies for other delivery vehicles, it has been seen that CBD degrades to THC and later to CBN under extreme conditions. However, the results of this study shows that CBD was not degraded to THC or later to CBN when extruded chewing gum was used as the delivery vehicle. This was highly surprising and indicates that CBD is better protected in an extruded chewing gum matrix.

Example 39

Preparation of Cannabinoid Chewing Gum Formulation with Specific Order

The time of addition of CBD 52% according to Example 13 was changed in this Example. While the time of addition was 8 minutes in Examples 13, the following additional time table was prepared in order to reveal the substantive meaning of the time of addition on the release of cannabinoids:

TABLE 3A

It was secured that CBD was thoroughly mixed into the composition and that a homogeneous mixture was obtained. Sugar alcohol* was prepared as a premix with CBD according to Example 9. Here, the content in weight % is calculated as the sugar alcohol content, excluding the CBD content in the premix. CBD 52%* was prepared according to Example 6. The chewing gum composition was abbreviated CG100 (Example 14). Specified order of addition in the preparation of chewing gum (CG100)

| Ingredient | Content in weight % | Application time in min. |
|---|---|---|
| CBD 52%* | 1 | 0 |
| CBD 52%* | 1 | 3 |
| CBD 52%* | 1 | 5 |
| CBD 52%* | 1 | 8 |
| CBD 52%* | 1 | 12 |
| Total | 13 | |

Example 40

Release of Cannabinoid from Extruded Chewing Gum

TABLE 3B

Chewing gum samples from Example 14 (CG100) was tested for release of CBD after 5 minutes of in vivo chewing according to the specification of Example 13. The test method of Example 24 was applied. The value indicates weight % of cannabinoid released from the chewing gum sample (CG).

| Application time in min. | Release % |
|---|---|
| 0 | 7 |
| 3 | 9 |
| 5 | 10 |
| 8 | 14 |
| 12 | 15 |

The result shows that release of the one or more cannabinoids may be dependent on the application order during the manufacturing process of extruded chewing gum. In this example, it was seen that application of the one or more cannabinoids after half the mixing time was favorable, just as long as the cannabinoids were homogeneously distributed in the extruded gum. The application time of 8 minutes in this example or even later was particularly favorable.

Example 41

Coating with CBD

TABLE 3C

Chewing gum samples from Example 23 was tested for release after 3 or 5 minutes of in vitro chewing according to the test method of Example 25. The value indicates weight % of cannabinoid released from the chewing gum sample (CG).

| CG Number | CG145 | CG146 |
|---|---|---|
| 3 minutes | 60 | 55 |
| 5 minutes | 59 | 61 |

The result was highly surprising since it was expected that a major amount of CBD from the coating was absorbed in the chewing gum upon chewing. However, the result shows that application of one or more cannabinoids into a coating, such as a hard coating, may be a promising way to deliver cannabinoids. Also, by combining the application of one or more cannabinoids in the coating as well as in the extruded chewing gum, controlled release of cannabinoids may be obtained. This may also be used to provide a biphasic release of cannabinoids, such that an initial high release is provided by the coating and a more sustained release is provided by incorporating the cannabinoids in the extruded chewing gum.

Example 42

CBD Delivered to the Oral Mucosa

Tests were conducted in accordance with the test method of Example 27. The tests were performed for CG100 and CG101. The values for the CBD content in saliva and in the chewing gum residue were measured after 5 min of chewing. From these values, the content of CBD delivered to the oral mucosa could be calculated.

TABLE 3D

Chewing gum samples from Example 14 were tested for content of CBD delivered to the oral mucosa after 5 minutes of in vivo chewing according to the test method of Example 27. The values indicate weight % of cannabinoid based on the one or more cannabinoids present in the initial formulation.

| CG Number | CG100 | CG101 |
|---|---|---|
| CBD in saliva | 0.1 | 0.1 |
| CBD in residue | 87 | 88 |
| CBD delivered to mucosa | 12.9 | 11.9 |

The results of the tests were very surprising as almost all CBD released after 5 minutes of chewing was delivered to the oral mucosa. It was expected that a much higher amount of CBD was present in the saliva after 5 minutes of chewing, but only a very low amount of CBD was found in the saliva. Based on the released amount of CBD (13% respective 12%), it could be calculated that <1% of the released CBD was present in the saliva and accordingly >99% CBD was delivered to the oral mucosa. Hence, the chewing gum formulation of the invention is very suitable for delivery of cannabinoids to the oral mucosa, much better than would have been expected.

Example 43

CBD Delivered to the Oral Mucosa

Tests were conducted in accordance with the test method of Example 27. The tests were performed for CG145 and CG146. The values for the CBD content in saliva and in the chewing gum residue were measured after 5 min of chewing. From these values, the content of CBD delivered to the oral mucosa could be calculated.

TABLE 3E

Chewing gum samples from Example 23 were tested for content of CBD delivered to the oral mucosa after 5 minutes of in vivo chewing according to the test method of Example 27. The values indicate weight % of cannabinoid based on the one or more cannabinoids present in the initial formulation.

| CG Number | CG145 | CG146 |
|---|---|---|
| CBD in saliva | 35 | 35 |
| CBD in residue | 40 | 45 |
| CBD delivered to mucosa | 25 | 30 |

The results of the tests were surprising as a very high amount of CBD released after 5 minutes of chewing was delivered to the oral mucosa. It was expected that a much higher amount of CBD was present in the saliva after 5 minutes of chewing. The total content of CBD delivered to the oral mucosa could be calculated to be about the double of the total content of CBD delivered to the oral mucosa when CBD was present in the chewing gum (Example 42) compared to the coating (Example 43). It was not expected that such a high content of CBD could be delivered to the oral mucosa with the present chewing gum formulation. In fact, the content of CBD would be higher if polysorbate was not applied in the coating suspension since polysorbate facilitates emulsifying properties of the saliva which prevent CBD to be delivered to the oral mucosa to an even higher degree.

By varying the content of CBD in the coating and the content of CBD in the chewing gum, a controlled delivery system may be established.

The invention claimed is:

1. A chewing gum for improved release of cannabinoids, the chewing gum being formulated as an extruded chewing gum comprising a chewing gum matrix of water-soluble chewing gum ingredients mixed into water-insoluble gum base, the extruded chewing gum being shaped into chewing gum pieces by rolling and scoring,
   the gum base comprising one or more natural resins in an amount of 10-40% by weight of the gum base, one or more elastomers in an amount of 3-30% by weight of the gum base, and one or more polyvinyl acetate elastomer plasticizers in an amount of 10-40% by weight of the gum base,
   wherein the weight-average molecular weight (Mw) of the one or more polyvinyl acetate elastomer plasticizers is from 5,000 to 40,000 q/mol,
   wherein the chewing gum matrix comprises one or more cannabinoids separated from cannabinoid plant material, and
   wherein the release rate of the one or more cannabinoids at a frequency of 60 chews per minute is at least 10% by weight of the one or more cannabinoids within the first 5 minutes upon oral administration.

2. The chewing gum according to claim 1, wherein the release rate of the one or more cannabinoids at a frequency of 60 chews per minute is between 10-50% by weight of the one or more cannabinoids within the first 5 minutes upon oral administration.

3. The chewing gum according to claim 1, wherein the release rate of the one or more cannabinoids at a frequency of 60 chews per minute is at most 30% by weight of the one or more cannabinoids within the first 5 minutes upon oral administration.

4. The chewing gum according to claim 1, wherein the release rate of the one or more cannabinoids is partly controlled by means of the composition of the water-insoluble gum base.

5. The chewing gum according claim 1, wherein the release rate of the one or more cannabinoids is partly controlled by means of the amount of the one or more natural resins.

6. The chewing gum according to claim 1, wherein the release rate of the one or more cannabinoids is partly controlled by means of the amount of the one or more elastomer plasticizers.

7. The chewing gum according to claim 1, wherein the release rate of the one or more cannabinoids is partly controlled by means of the water-soluble chewing gum ingredients.

8. The chewing gum according to claim 1, wherein the release rate of the one or more cannabinoids is partly controlled by means of the location of the one or more cannabinoids in the chewing gum.

9. The chewing gum according claim 1, wherein the one or more cannabinoids is further comprised in an outer coating of the extruded chewing gum.

10. The chewing gum according to claim 1, wherein the release rate of the one or more cannabinoids is partly controlled by means of further release enhancing ingredients.

11. The chewing gum according to claim 1, wherein at least 10% by weight of the one or more cannabinoids is present in unbound form.

12. The chewing gum according claim 1, wherein the one or more elastomer plasticizers is present in an amount of 15-35% by weight of the gum base.

13. The chewing gum according to claim 1, wherein the gum base comprises less than 50% of gum base polymers.

14. The chewing gum according to claim 1, wherein the one or more natural resins is present in an amount of 15-35% by weight of the gum base.

15. The chewing gum according to claim 1, wherein the one or more cannabinoids comprises one or more cannabinoids selected from the group consisting of cannabidiol (CBD), cannabidiolic acid (CBDA), cannabidivarin (CBDV), salts and derivatives thereof.

16. The chewing gum according to claim 1, wherein the one or more cannabinoids comprises one or more cannabinoids selected from the group consisting of tetrahydrocannabinol (THC), tetrahydrocannabinolic acid (THCA), tetrahydrocannabivarin (THCV), salts and derivatives thereof.

17. The chewing gum according to claim 1, wherein the one or more cannabinoids comprises cannabigerol (CBG), salts and derivatives thereof.

18. The chewing gum according claim 1, wherein the one or more cannabinoids comprises at least two cannabinoids.

19. The chewing gum according to claim 1, wherein the one or more cannabinoids is present in a pre-mixture with one or more sugar alcohols or saccharose.

20. The chewing gum according to claim 1, wherein the one or more cannabinoids comprises at least one water-soluble cannabinoid.

21. The chewing gum according claim 1, wherein the chewing gum comprises a self-emulsifying agent.

22. A chewing gum for improved release of cannabinoids, the chewing gum being formulated as an extruded chewing gum comprising a chewing gum matrix of water-soluble chewing gum ingredients mixed into water-insoluble gum base,
   the gum base comprising one or more natural resins in an amount of 10-40% by weight of the gum base, one or more elastomers in an amount of 3-30% by weight of the gum base, and one or more polyvinyl acetate elastomer plasticizers in an amount of 10-40% by weight of the gum base, the extruded chewing gum being shaped into chewing gum pieces by rolling and scoring,
   wherein the weight-average molecular weight (Mw) of the one or more polyvinyl acetate elastomer plasticizers is from 5,000 to 40,000 q/mol,
   wherein the chewing gum matrix comprises one or more cannabinoids extracted from cannabinoid plant material, and
   wherein the release rate of the one or more cannabinoids at a frequency of 60 chews per minute is at least 10% by weight of the one or more cannabinoids within the first 5 minutes upon oral administration.

23. A chewing gum for improved release of cannabinoids, the chewing gum being formulated as an extruded chewing gum comprising a chewing gum matrix of water-soluble chewing gum ingredients mixed into water-insoluble gum base,
   the gum base comprising one or more natural resins in an amount of 10-40% by weight of the gum base, one or more elastomers in an amount of 3-30% by weight of the gum base, and one or more polyvinyl acetate elastomer plasticizers in an amount of 10-40% by weight of the gum base,
   wherein the weight-average molecular weight (Mw) of the one or more polyvinyl acetate elastomer plasticizers is from 5,000 to 40,000 q/mol,
   wherein the chewing gum matrix comprises one or more cannabinoids, wherein the release rate of the one or more cannabinoids is at least 10% by weight of the one or more cannabinoids within the first 5 minutes upon oral administration, and wherein the release rate of the one or more cannabinoids is partly controlled by means of the composition of the water-insoluble gum base.

24. The chewing gum according claim 23, wherein the release rate of the one or more cannabinoids is partly controlled by means of the amount of the one or more natural resins comprised in the water-insoluble gum base.

25. The chewing gum according claim 23, wherein the release rate of the one or more cannabinoids is partly controlled by means of the amount of the one or more elastomer plasticizers comprised in the water-insoluble gum base.

26. A chewing gum for improved release of cannabinoids, the chewing gum being formulated as an extruded chewing gum comprising a chewing gum matrix of water-soluble chewing gum ingredients mixed into water-insoluble gum base, the gum base comprising one or more natural resins in an amount of 10-40% by weight of the gum base, one or more polyvinyl acetate elastomers in an amount of 3-30% by weight of the gum base, and one or more elastomer plasticizers in an amount of 10-40% by weight of the gum base, wherein the weight-average molecular weight (Mw) of the one or more polyvinyl acetate elastomer plasticizers is from 5,000 to 40,000 g/mol, wherein the chewing gum matrix comprises one or more cannabinoids, wherein the release rate of the one or more cannabinoids is at least 10% by weight of the one or more cannabinoids within the first 5 minutes upon oral administration, and wherein the release rate of the one or more cannabinoids is partly controlled by means of the water-soluble chewing gum ingredients.

* * * * *

UNITED STATES PATENT AND TRADEMARK OFFICE
CERTIFICATE OF CORRECTION

PATENT NO. : 11,013,685 B2
APPLICATION NO. : 16/257785
DATED : May 25, 2021
INVENTOR(S) : Heidi Ziegler Bruun et al.

It is certified that error appears in the above-identified patent and that said Letters Patent is hereby corrected as shown below:

In the Claims

Column 45, Claim 1, Line 15:
"is from 5,000 to 40,000 q/mol"
Should be changed to:
-- is from 5,000 to 40,000 g/mol --

Column 46, Claim 22, Line 44:
"is from 5,000 to 40,000 q/mol"
Should be changed to:
-- is from 5,000 to 40,000 g/mol --

Column 46, Claim 23, Line 65:
"is from 5,000 to 40,000 q/mol"
Should be changed to:
-- is from 5,000 to 40,000 g/mol --

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*